US009017680B2

(12) United States Patent
Fischkoff et al.

(10) Patent No.: US 9,017,680 B2
(45) Date of Patent: *Apr. 28, 2015

(54) METHODS OF ADMINISTERING ANTI-TNFα ANTIBODIES

(71) Applicant: AbbVie Biotechnology Ltd., Hamilton (BM)

(72) Inventors: Steven A. Fischkoff, Short Hills, NJ (US); Joachim Kempeni, Neustadt (DE); Roberta Weiss, Wynnewood, PA (US)

(73) Assignee: AbbVie Biotechnology Ltd., Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 14/542,529

(22) Filed: Nov. 14, 2014

(65) Prior Publication Data

US 2015/0071939 A1    Mar. 12, 2015

Related U.S. Application Data

(63) Continuation of application No. 10/163,657, filed on Jun. 5, 2002, now Pat. No. 8,889,135.

(60) Provisional application No. 60/296,961, filed on Jun. 8, 2001.

(51) Int. Cl.
*A61K 39/395* (2006.01)
*C07K 16/24* (2006.01)
*A61K 39/00* (2006.01)

(52) U.S. Cl.
CPC ......... *C07K 16/241* (2013.01); *C07K 2317/565* (2013.01); *C07K 2317/21* (2013.01); *C07K 2317/76* (2013.01); *A61K 2039/505* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 5,231,024 A | 7/1993 | Moeller et al. | |
| 5,336,181 A | 8/1994 | Nakao et al. | |
| 5,654,407 A | 8/1997 | Boyle et al. | |
| 5,698,195 A | 12/1997 | Le | |
| 5,705,389 A | 1/1998 | Braham et al. | |
| 5,795,967 A | 8/1998 | Aggarwal et al. | |
| 5,859,205 A | 1/1999 | Adair et al. | |
| 5,877,293 A | 3/1999 | Adair et al. | |
| 5,929,212 A | 7/1999 | Jolliffe et al. | |
| 5,945,098 A | 8/1999 | Sarno | |
| 5,994,510 A | 11/1999 | Adair et al. | |
| 6,015,557 A | 1/2000 | Tobinick | |
| 6,024,938 A | 2/2000 | Corbo et al. | |
| 6,090,382 A | 7/2000 | Salfeld | |
| 6,171,586 B1 | 1/2001 | Lam et al. | |
| 6,214,870 B1 | 4/2001 | McClure et al. | |
| 6,235,281 B1 | 5/2001 | Stenzel et al. | |
| 6,258,562 B1 | 7/2001 | Salfeld et al. | |
| 6,270,766 B1 | 8/2001 | Feldman et al. | |
| 6,423,321 B2 | 7/2002 | Tobinick | |
| 6,509,015 B1 | 1/2003 | Salfeld et al. | |
| 6,537,549 B2 | 3/2003 | Tobinick | |
| 6,562,006 B1 | 5/2003 | Hjertman et al. | |
| 7,153,507 B2 | 12/2006 | van de Winkel et al. | |
| 7,223,394 B2 | 5/2007 | Salfeld et al. | |
| 7,250,165 B2 | 7/2007 | Heavner et al. | |
| 7,863,426 B2 | 1/2011 | Wan et al. | |
| 7,919,264 B2 | 4/2011 | Maksymowych et al. | |
| 8,889,135 B2 * | 11/2014 | Fischkoff et al. | 424/145.1 |
| 2001/0004456 A1 | 6/2001 | Tobinick | |
| 2001/0016195 A1 | 8/2001 | Tobinick | |
| 2001/0026801 A1 | 10/2001 | Tobinick | |
| 2003/0012786 A1 | 1/2003 | Teoh et al. | |
| 2003/0049725 A1 | 3/2003 | Heavner | |
| 2003/0092059 A1 | 5/2003 | Salfeld et al. | |
| 2003/0161828 A1 | 8/2003 | Abdelghany et al. | |
| 2003/0219438 A1 | 11/2003 | Salfeld et al. | |

(Continued)

FOREIGN PATENT DOCUMENTS

| | | |
|---|---|---|
| CA | 2243459 | 8/1997 |
| CA | 2261630 | 2/1998 |

(Continued)

OTHER PUBLICATIONS

Felson et al., Arthritis & Rheumatism vol. 41, No. 9, Sep. 1998, pp. 1564-1570.*
Wolfe et al. (J Rheumatol. Jun. 2001;28(6):1423-30 which was presented in Chicago, Illinois, USA, Feb. 17-18, 2000 as part of the Symposium Proceedings: Changing Goals for Rheumatoid Arthritis Treatment: Evidence and Insight).*
Chandry 2000, "D2E7," *Current Opinion in Anti-Inflammatory & Immunomodulatory Investigational Drugs* 2(1):31-34.
Rutgeerts 1999, "Review article: efficacy of infliximab in Chron's disease—induction and maintenance of remission," *Ailment Pharmacol Ther* 13(Suppl 4):9-15.
Targan, et al., 1997 "A Short-Term Study of Chimeric Monoclonal Antibody cA2 to Tumor Necrosis Factor α for Crohn's Disease," *N. Engl J. Med.* 337(15):1029-1035.

(Continued)

*Primary Examiner* — Zachary Skelding
(74) *Attorney, Agent, or Firm* — Dechert LLP

(57) ABSTRACT

Methods of treating disorders in which TNFα activity is detrimental via biweekly, subcutaneous administration of human antibodies, preferably recombinant human antibodies, that specifically bind to human tumor necrosis factor α (hTNFα) are disclosed. The antibody may be administered with or without methotrexate. These antibodies have high affinity for hTNFα (e.g., $K_d=10^{-8}$ M or less), a slow off rate for hTNFα dissociation (e.g., $K_{off}=10^{-3}$ sec$^{-1}$ or less) and neutralize hTNFα activity in vitro and in vivo. An antibody of the invention can be a full-length antibody or an antigen-binding portion thereof. Kits containing a pharmaceutical composition and instructions for dosing, and preloaded syringes containing pharmaceutical compositions are also encompassed by the invention.

4 Claims, 6 Drawing Sheets

(56) References Cited

U.S. PATENT DOCUMENTS

| | | |
|---|---|---|
| 2003/0235585 A1 | 12/2003 | Fischkoff et al. |
| 2004/0009172 A1 | 1/2004 | Fischkoff et al. |
| 2004/0033228 A1 | 2/2004 | Krause et al. |
| 2004/0120952 A1 | 6/2004 | Knight et al. |
| 2004/0126372 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0219142 A1 | 11/2004 | Banerjee et al. |
| 2005/0123541 A1 | 6/2005 | Heavner et al. |
| 2005/0249735 A1 | 11/2005 | Le et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0153846 A1 | 7/2006 | Krause et al. |
| 2006/0246073 A1 | 11/2006 | Knight et al. |
| 2007/0003548 A1 | 1/2007 | Heavner et al. |
| 2007/0041905 A1 | 2/2007 | Hoffman et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0196373 A1 | 8/2007 | Le et al. |
| 2007/0202104 A1 | 8/2007 | Banerjee et al. |
| 2007/0249813 A1 | 10/2007 | Salfeld et al. |
| 2007/0292442 A1 | 12/2007 | Wan et al. |
| 2007/0298040 A1 | 12/2007 | Le et al. |
| 2008/0025976 A1 | 1/2008 | Le et al. |
| 2009/0148513 A1 | 6/2009 | Fraunhofer et al. |
| 2009/0280065 A1 | 11/2009 | Willian et al. |
| 2010/0034823 A1 | 2/2010 | Borhani et al. |
| 2010/0040604 A1 | 2/2010 | Salfeld et al. |
| 2010/0160894 A1 | 6/2010 | Julian et al. |
| 2010/0278822 A1 | 11/2010 | Fraunhofer et al. |
| 2011/0002935 A1 | 1/2011 | Wan et al. |
| 2011/0054414 A1 | 3/2011 | Shang et al. |
| 2011/0171227 A1 | 7/2011 | Okun et al. |
| 2011/0300151 A1 | 12/2011 | Okun et al. |

FOREIGN PATENT DOCUMENTS

| | | | |
|---|---|---|---|
| EP | | 351789 A2 | 1/1990 |
| EP | | 366043 A1 | 5/1990 |
| EP | | 492448 A1 | 7/1992 |
| EP | | 186833 B2 | 8/1992 |
| EP | | 212489 B1 | 11/1994 |
| EP | | 101681 B1 | 12/1994 |
| EP | | 659766 A1 | 6/1995 |
| EP | | 614984 B1 | 8/2001 |
| EP | | 1174148 | 1/2002 |
| EP | | 1232753 A1 | 8/2002 |
| EP | | 1254666 A1 | 11/2002 |
| EP | | 1406656 B1 | 1/2013 |
| GB | | 2279077 A | 12/1994 |
| HU | | 211626 | 12/1995 |
| HU | | 215242 | 11/1998 |
| WO | WO 91/02078 A1 | | 2/1991 |
| WO | WO 91/04054 A1 | | 4/1991 |
| WO | WO 91/09967 A1 | | 7/1991 |
| WO | WO 92/11383 A1 | | 7/1992 |
| WO | WO 92/16553 A1 | | 10/1992 |
| WO | WO 93/06213 A1 | | 4/1993 |
| WO | WO 93/11793 A1 | | 6/1993 |
| WO | WO 94/29347 A1 | | 12/1994 |
| WO | WO 95/23813 A1 | | 9/1995 |
| WO | WO 97/04801 A1 | | 2/1997 |
| WO | WO 9729131 A1 * | | 8/1997 |
| WO | WO 98/04281 A1 | | 2/1998 |
| WO | WO 98/05357 A1 | | 2/1998 |
| WO | WO 98/56418 A1 | | 12/1998 |
| WO | WO 00/51637 A1 | | 9/2000 |
| WO | WO 01/00229 A1 | | 1/2001 |
| WO | WO 01/37874 A2 | | 5/2001 |
| WO | WO 01/47554 A1 | | 7/2001 |
| WO | WO 01/94585 A1 | | 12/2001 |
| WO | WO 02/12502 A2 | | 2/2002 |
| WO | WO 02/096461 A1 | | 12/2002 |
| WO | WO 02/100330 A3 | | 12/2002 |
| WO | WO 03/080672 A1 | | 10/2003 |
| WO | WO 2006/041970 A2 | | 4/2006 |

OTHER PUBLICATIONS

Chey 2001, "Infliximab for Patients With Refractory Ulcerative Colitis," *Inflamm Bowel Dis.* 7(Supp.1):S30-S33.

Haynes et al., 1998, "A comparison of the disease-modifying and cytokine-regulating activities of tenidap, piroxicam and cyclosporin-A using the adjuvant-induced model of arthritis in rats," *Inflammopharmacology* 6(3):193-202.

Lichtenstein 2001, "Commentary. Is infliximab effective for induction of remission in patients with ulcerative colitis?" *Inflamm Bowel Dis.* 7(2):89-93.

Prupas et al., 1996, "Tenidap in patients with Rheumatoid arthritis: A 4-week, placebo-controlled study," *Scand J Rheumatology* 25(6):345-351.

Sands et al., 2001, "Infliximab in the treatment of severe, steroid-refractory ulcerative colitis: A pilot study," *Inflamm Bowel Dis.* 7(2):83-88.

Abraham et al., 1995, "Efficacy and Safety of Monoclonal Antibody to Human Tumor Necrosis Factor α in Patients with Sepsis Syndrome," *JAMA* 273(12): 934-941.

Abraham, 1998, "Cytokine modifiers: pipe dream or reality?" Chest Mar. 1998 LNKD-PubMed:9515897 113(3) Suppl 224S-227S.

Arthur et al., 1999, "Safety of self-injection of gold and methotrexate," *J Rheumatol* 26(2):302-305.

Aulton, 2001, Pharmaceutics: The Science of Dosage Form Design, $2^{nd}$ Ed., pp. 275-288.

Barbuto et al., 1993, "Production of Neutralizing Antibodies to Tumor Necrosis Factor by Human Tumor-Infiltrating B Lymphocytes," *Proc Am Assoc Cancer Res* 34:487 (abstract 2904).

Barrera et al., 1999, "Effect of a Fully Human Anti-TNFα Monoclonal Antibody on the Local and Systemic Expression of TNFα and IL-18," *Arthritis Rheum* 42(Suppl 9):S75.

Barrera et al., 2001, "Effects of Treatment with a Fully Human Anti-Tumor Necrosis Factor α Monoclonal Antibody on the Local and Systemic Homeostasis of Interleukin 1 and TNFα in Patients with Rheumatoid Arthritis," *Ann Rheum Dis* 60(7):660-669.

Barrera et al., 2002,"Drug survival, efficacy and toxicity of monotherapy with a fully human anti-tumour necrosis with a fully human anti-tumour necrosis factor-α antibody compared with methotrexate in long-standing rheumatoid arthritis," *Rheumatology* 41:430-439.

BASF, Pharma Letter, 1999, "Positive data with CAT, BASF arthritis drug," p. 1.

BASF, Pharma Letter, 2000, "BASF moves into phase III with D2E7," p. 1.

BASF, Pharma Letter, 2000, "BASF sees D2E7 filing next year; potential against Enbrel," pp. 1-2.

Bendtzen et al., 1990, "Auto-Antibodies to IL-1α and TNFα in Normal Individuals and in I nfectious and Immunoinflammatory Disorders," The Physiological and Pathological Effects of Cytokines, Wiley-Liss, Inc., pp. 447-452.

Bodansky & Latner (eds.), 1973, Advances in Clinical Chemistry, Academic Press, vol. 16, p. 63.

Boekstegers et al, 1994, "Repeated administration of a F(ab')2 fragment of an anti-tumor necrosis factor α monoclonal antibody in patients with severe sepsis: effects on the cardiovascular system and cytokine levels," *Shock* 1(4):237-245.

Bombardier et al., 2002, "Pattern of DMARD use in a North American Cohort of Patients with Early Rheumatoid Arthritis (RA) (Sonora)," *Arthritis Rheum* 46(Suppl 9):S344.

Borigini et al., 1995, "Innovative Treatment Approaches for Rheumatoid Arthritis: Combination Therapy," *Baillière's Clinical Rheumatology* 9(4): 689-710.

(56) References Cited

OTHER PUBLICATIONS

Boyle et al., 1993, "A Novel Monoclonal Human IgM Autoantibody which Binds Recombinant Human and Mouse Tumor Necrosis Factor-α" *Cell Immunol* 152:556-568.
Boyle et al., 1993, "The B5 Monoclonal Human Autoantibody Binds to Cell Surface TNFα on Human Lymphoid Cells and Cell Lines and Appears to Recognize a Novel Epitope" *Cell Immunol* 152:569-581.
Breedveld et al., 2001, "The Fully Human Anti-TNF Antibody Adalim umab (D2E7) in Combination with Methotrexate (MTX) in the Treatment of Active Rheumatoid Arthritis: Results of a 2-Year Study," Presented at: *The Annual Meeting of the European League Against Rheumatism (EULAR)*, Prague, Czech Republic, Jun. 2001.
Breedveld et al., 2002, "The Long-term Efficacy and Safety of Adalim umab (D2E7), the Fully Human Anti-TNF Monoclonal Antibody, in Combination with Methotrexate in the Treatment of Rheumatoid Arthritis: Results of a 2-Year Study," *J Clin Rheumatol* 8(Suppl 3):S46.
Breedveld et al., 2006, "A Multicenter, Ran domized, Double-Blind Clinical Trial of Combination Therapy With Adalimumab Plus Methotrexate Versus Methotrexate Alone or Adalim umab Alone in Patients With Early, Aggressive Rheumatoid Arthritis Who Had Not Had Previous Methotrexate Treatment," *Arthritis Rheum* 54(1):26-37.
Bresnihan et al., 2001, "The safety and efficacy of interleukin-1 receptor antagonist in the treatment of rheumatoid arthritis," *Semin Arthritis Rheum* 30(5) (Suppl 2):17-20.
Burmester et al., 2002, "Long-Term Efficiacy and Safety of Adalim umab (D2E7) Monotherapy in Patients With DMARD-Refractory Rheumatoid Arthritis—Results From a 2-Year Study," *Arthritis Rheum* 46(Suppl 9):S537.
Burmester et al., 2013, "Efficacy, Pharmacokinetics, and Safety of Different Doses of Methotrexate in Combination With Adalimumab: Results from the CONCERTO Trial," *Ann Rheum Dis* 72(Suppl 3):72 (abstract OP0067).
Cambridge Antibody Technology Group, PLLC, 1998, "Impressive clinical data with CAT/BASF human antibody in rheumatoid arthritis," Press Release, pp. 1-2.
Case, 2001, "Old and New Drugs Used in Rheumatoid Arthritis: A Historical Perspective," *Am J Ther* 8:163-179.
Center for Drug Evaluation and Research and Center for Biologics Evaluation and Research, Application No. 125057.0, Statistical review(s) for Abbott Lab's adalimumab in the treatment of rheumatoid arthritis, Nov. 12, 2002, pp. 1-27.
Chikanza & Sakkas, 2000, "Advances in the Therapy of Rheumatoid Arthritis with Biological Agents" *Emerging Drugs* 5(4):367-384.
Chow et al., 1994, "Effect of monoclonal antibody on human tumor necrosis factor (TNF MAb) on TNFα, IL-1β, and IL-6 levels in patients with sepsis syndrome," *Clinical Research* 42(2):299A.
Cleland et al., 2001, "A specific molar ratio of stabilizer to protein is required for storage stability of a lyophilized monoclonal antibody," *J Pharm Sci* 90(3):310-321.
Coe et al., 2011, "Population differences in proinflammatory biology: Japanese have healthier profiles than Americans," *Brain Behav Immun* 25(3):494-502.
Cohen et al., 1996, "Intersept: An international, multicenter, placebo-controlled trial of monoclonal anitbody to human tumor necrosis factor-α in patients with sepsis," *Crit Care Med* 24(9):1431-1440.
CONCERTO clinical trial information, PDF excerpt from https://www.clinicaltrialregister.eu on study NCT01185301 (as submitted to EPO on Oct. 9, 2013), pp. 1-18 of PDF.
Cox et al. 1994,"A directory of human germ-line $V_K$ segments reveals a strong bias in their usage," *Eur J Immunol* 24(2):827-836.
Davis et al. 1995, "Preclinical pharmacokinetic evaluation of the respiratory syncytial virus-specific reshaped human monoclonal antibody RSHZ19," *Drug Metab Dispos* 23(10):1028-1036.
den Broeder et al., 1998, "The Effect of D2E7, a New Human Anti-TNFα Monoclonal Antibody, on the Oxidative Burst of PMN in Patients with RA," *Arthritis Rheum* 41(9):S57 No. 150.
den Broeder et al., 2002, "A Single Dose, Placebo Controlled Study of the Fully Human Anti-Tumor Necrosis Factor-α Antibody Adalimumab (D2E7) in Patients with Rheumatoid Arthritis," *J Rheumatol* 29(11):2288-2298.
den Broeder et al., 2002, "Long term anti-tumour necrosis factor α monotherapy in rheumatoid arthritis: effect on radiological course and prognostic value of markers of cartilage turnover and endothelial activation," *Ann Rheum Dis* 61:311-318.
Department of Surgery, University of Toronto, Annual Report (1998-1999), pp. 1-326.
Detournay et al., 1998, "Prefilled disposable syringes vs. conventional injection systems: European Medico economic analysis," *Eur J Hosp Pharm* 4(4):109-113.
Duma et al., 1992, "Pharmaceutical Dosage Forms: Parenteral Medications," Marcel Dekker, Inc., vol. 1., $2^{nd}$ Ed., pp. 21-26.
Egan et al., 1998, "A Randomized, Single-Blind, Pharmacokinetic and Dose Response Study of Subcutaneous Methotrexate, 15 and 25 mg/wk, for Refractory Ulcerative Colitis and Crohn's Disease," *Gastroenterology* 114(Suppl1):A970-A971 (abstract G3 978).
Eissner et al., 2000, "Naive Monocytes Can Trigger Transendothelial Migration of Peripheral Blood Cells Through the Induction of Endothelial Tumor Necrosis Factor-α," *Scand J Immunol* 51:251-261.
Elliott et al., 1993, "Treatment of rheumatoid arthritis with chimeric monoclonal antibodies to tumor necrosis factor α," *Arthritis Rheum* 36(12):1681-90.
Elliott et al., 1995, "TNFα Blockade in Rheumatoid Arthritis: Rationale, Clinical Outcomes and Mechanisms of Action," *Intl J Immunopharmac* 17(2):141-145.
European Medicines Agency, 2004, "Scientific Discussion," Prescribing Info for HUMIRA®, pp. 1-25.
European Medicines Agency, "Summary of Product Characteristics," Humira®, accessed on Aug. 13, 2013, pp. 1-240.
Emery et al., 1999, "Targeted therapies in rheumatoid arthritis: the need for action," *Rheumatology* (Oxford) 38(10):911-912.
Emery et al., 2001, "Changes in Pro-MMP-1 in Relation to Standard Measures of Disease Activity Over a 6 Month Treatment Period with Adalim umab (D2E7) in Rheumatoid Arthritis," *Arthritis Rheum* 44(9):S215.
Fautrel et al., 2000, "Interest of anti-TNF-α treatment in inflammatory and infectious diseases," *Rev Med Interne* 21:872-888.
FDA Prescription info for Humira® (Revised Sep. 2012), pp. 1-46.
FDA Prescription info for Humira® (Revised May 2013), pp. 1-55.
FDA summary of product characteristics of Humira® (adalim umab) (2002) pp. 1-16.
Feldmann et al., 2001, "Anti-TNFα Therapy of Rheumatoid Arthritis: What Have We Learned," *Annu Rev Immunol* 19:163-196.
Figini et al., 1994, "In Vitro Assembly of Repertoires of Antibody Chains on the Surface of Phage by Renaturation," *J Mol Biol* 239:68-78.
Fomsguaard et al., 1989, "Auto-antibodies to Tumor Necrosis Factor α in Healthy Humans and Patients with Inflammatory Diseases and Gram-Negative Bacterial Infections," *Scand J Immunol* 30:219-223.
Foote & Winter, 1992, "Antibody Framework Residues Affecting the Conformation of the Hypervariable Loops," *J Mol Biol* 224(2):487-499.
Furst et al., 2002, "Safety and Efficacy of Adalimumab (D2E7), a Fully Human Anti-TNF-α Monoclonal Antibody, Given in Combination with Standard Antirheumatic Therapy: Safety Trial of Adalim umab in Rheumatoid Arthritis," *Arthritis Rheum* 46(Suppl 9):S572.
Furst et al., 2002, "Safety and Efficacy of Adalimumab (D2E7), a Fully Human Anti-TNF-α Monoclonal Antibody, Given in Combination with Standard Antirheumatic Therapy: Safety Trial of Adalim umab in Rheumatoid Arthritis (STAR)," *Ann Rheum Dis* 61(Suppl 1): S572.
Furst et al., 2001, "TNF Blockade by the Fully Human Monoclonal Antibody Adalimumab (D2E7), in the Armada Trial Results in Decreases in Serum Matrix Metalloproteinase (MMP) Levels Along with Impressive Clinical Improvement in Refractory RA Patients," *Arthritis Rheum* 44(Suppl 9):S215.

(56) References Cited

OTHER PUBLICATIONS

Gallagher et al., 2001, "A multicenter, open-label, prospective, randomized, dose-ranging pharmacokinetic study of the anti-TNF-α antibody afel imomab in patients with sepsis syndrome," *Intensive Care Med* 27(7):1169-78.
Giuliani et al., 2001, "Serum interleuk in-6, soluble interleukin-6 receptor and soluble gp130 exhibit different patterns of age- and menopause-related changes," *Experimental Gerontology* 36:547-557.
Goto & Sumida, 2002 "[Adalimumab]," English abstract Medline abstract NLM12510366, p. 1.
Goto & Sumida, 2002, "[Adalimumab],"*Nihon Rinsho* 60(12):2384-2389 (in Japanese).
Griffiths et al., 1993,"Human anti-self antibodies with high specificity from phage display libraries," *The EMBO J* 12(2):725-734.
Grubb, 1994, "Human immunoglobulin all otypes and Mendelian polymorphism of the human immunoglobulin genes," in Oss C.J., Regenmortel M.H.V. (eds): Immunochemistry, New York, Dekker, pp. 47-68, see pp. 47-55.
Hawkins et al., 1992, "Selection of Phage Antibodies by Binding Affinity Mim icking Affinity Maturation," *J Mol Bio* 226:889-896.
Hillgren et al., 2002, "Protection mechanism of Tween 80 during freeze-thawing of a model protein, LDH," *Intl J Pharmaceutics* 237 (1-2) 57-69.
Holler et al., 1995, "Modulation of Acute Graft-Versus-Host Disease After Allogeneic Bone Marrow Transplantation by Tumor Necrosis Factor α (TNFa) Release in the Course of Pretransplant Conditioning: Role of Conditioning Regimens and Prophylactic Application of a Monoclonal Antibody Neutralizing Human TNFa (MAK 195F)," *Blood* 86(3):890-899.
Holliger et al., 2005, "Engineered antibody fragments and the rise of single domains," *Nat Biotechnol* 23(9):1126-36.
Holt et al., 2003, "Domain Antibodies: Proteins for Therapy," *Trends in Biotech* 21(11): 484-490.
Hoogenboom et al., 1996, "Converting rodent into human antibodies by guided selection," *Antibody Engineering*, Oxford University Press, Ch. 8, pp. 169-185.
Huse et al., 1989, "Generation of a large combinatorial library of the immunoglobulin repertoire in phage lambda," *Science* 246:1275-81.
Ikezu & Gendelman, 2008, "Autoimmune Diseases," Springer, *Neuroimmune Pharmacology*, p. 283.
Janeway et al., 1997, "The protein products of MHC class I and class II genes are highly polymorphic," *Immunobiology*, 3rd Ed., pp. 4:24-4:30.
Janeway et al., 2001, *Immunobiology*, 5th Ed., Garland Science, pp. 94-105.
Jespers et al., 1994, "Guiding the Selection of Human Antibodies from Phage Display Repertoires to a Single Epitope of an Antigen," *Bio/Technology* 12:899-903.
Jones, 2013, Declaration in opposition proceedings to EP 1 406 656, pp. 1-3.
Jorgensen et al., 1998, "Interleukin-4 and Interleukin-10 are Chondroprotective and Decreases Mononuclear Cell Recruitment in Human Rheumatoid Synovium in vivo," *Immunol* 93(4):518-523.
Kanakoudi-Tsakalidou et al., 2001, "Influenza vaccination in children with chronic rheumatic diseases and long-term immunosuppressive therapy," *Clin Exp Rheumatol* 19:589-594.
Kavanaugh, 1998, "Anti-Tumor Necrosis Factor-α Monoclonal Antibody Therapy for Rheumatoid Arthritis," *Emerging Therapeutics* 24(3):593-614.
Kavanaugh et al., 2002, "The Armada Trial: 12-Month Efficacy and Safety of Combination Therapy with Adalim umab (D2E7), the First Fully Human Anti-TNF Monoclonal Antibody, and Methotrexate (MTX) in Patients with Active Rheumatoid Arthritis," *Ann Rheum Dis* 61(Suppl I):S168.
Kavanaugh et al., 2002, "Treatment with Adalimumab (D2E7) does not Affect Normal Immune Responsiveness," *Arthritis Rhe um* 46(Suppl 9):S132.
Kaymakcalan et al., 2002, "Comparison of Adalimumab (D2E7), Infliximab, and Etanercept in the Prevention of Polyarthritis in the Transgene Murine Model of Rheumatoid Arthritis," *Arthritis Rheum* 46(Suppl 9):S304.
Kem peni, 1999, "Preliminary Results of Early Clinical Trials with the Fully Human Anti-TNFα Antibody D2E7," *Ann Rheum Dis* 58(Suppl I:170-172.
Kem peni, 2000, "Update on D2E7: a Fully Human Anti-Tumor Necrosis Factor α Monoclonal Antibody," *Ann Rheum Dis* 59(Suppl I):144-145.
Keystone et al., 2001, "The ARMADA Trial: A Double-Blind Placebo Controlled Trial of the Fully Human Anti-TNF Monoclonal Antibody Adalim umab (D2E7) in Patients with Active RA on Methotrexate (MTX)," *Arthritis Rheum* 44(Suppl 9):S213 (abstract 965).
Keystone et al., 2001, "The Fully Human Anti-TNF Monoclonal Antibody Adalimumab (D2E7), dose ranging study: the 24-week Clinical Results in Patients with Active RA on Methotrexate Therapy (the ARMADA trial)," Presen ted at *European League Against Rheumatism—Annual Congress* (abstract OP0086), pp. 1-2.
Keystone et al., 2002, "Efficacy and safety of adalimumab (D2E7), the fully human anti-tnf monoclonal antibody, in MTX partial responders: Results of the 24-week ARMADA trial," *J Clin Rheumatol* 9(Suppl 3):569.
Keystone at al., 2003, "Subgroup Analysis of Radiographic Progression in RA Patients Treated with Adalimumab," *Ann Rheum Dis* 62(Suppl I):169 (Poster THU0198).
Kobelt et al., 2003, "The Cost-Effectiveness of Infliximab (Remicade) in the Treatment of Rheumatoid Arthritis in Sweden and the United Kingdom based on the ATTRACT Study," *Rheumatol* 42(2)326-335.
Kremer et al., 2001 "Rational Use of New and Existing Disease-Modifying Agents in Rheumatoid Arthritis," *Ann Intern Med* 134:695-706.
Kupper, 2008, declaration during examination of EP 1 406 656, pp. 1-3.
Lerner at al., 1992, "Antibodies without immunization," *Science* 258:1313-1314.
The Lenercept Multiple Sclerosis Study Group and the University of British Columbia MS/MRI Analysis Group, 1999, "TNF neutralization in MS: Results of a randomized, placebo-controlled multicenter study," *Neurology* 53(3):457-465.
Leusch et al., 1991, "Failure to demonstrate TNFa-specific autoantibodies in human sera by ELISA and Western blot," *J Immunol Methods* 139:145-147.
Levine, 2000 "Pharmacology: Drug Actions and Reactions," Parthenon, 6th Ed. pp. 99-102.
Lewis et al., 1994, "Use of alanine scanning mutagenesis to improve the affinity of an anti$_{gp}$120 (HIV) antibody," *J Cell Biochem* 18D:215.
Linder et al., 1997, "Peripheral Blood Mononuclear Cells Invade Programmed Cell Death in Human Endothelial Cells and May Prevent Repairs; Role of Cytokines," *Blood* 89(6):1931-1938.
Lipsky et al., 2000,"Infliximab and Methotrexate in the Treatment of Rheumatoid Arthritis," *N Engl J Med* 343:1594-1602.
Lorenz, 2002, "Technology Evaluation: Adalimumab, Abbott Laboratories," *Curr Op Mol Ther* 4(2):185-190.
Low, 1996, thesis extract, Cambridge University, p. 1 of extract.
Low et al., 1996, "Mim icking Somatic Hypermutation: Affinity Maturation of Antibodies Displayed on Bacteriophage Using a Bacterial Mutator Strain," *J Mol Biol* 260:359-368.
Mailer et al., 1990,"Monoclonal antibodies to human tumor necrosis factor α: in vitro and vivo application," *Cytokine* 2(3):162-69.
Maini et al. , 1998, "Therapeutic efficacy of multiple intravenous infusions of anti-tumor necrosis factor α monoclonal antibody combined with low-dose weekly methotrexate in rheumatoid arthritis," *Arthritis Rheum* 41(9):1552-1563.
Maini et al., 1999, "Infliximab (chimeric anti-tumour necrosis factor α monoclonal antibody) versus placebo in rheumatoid arthritis patients receiving concomitant methotrexate: a randomized phase III trial," *Lancet* 354:1932-1939.
"The Major Components of Blood" Website (May 12, 2001, pp. 1-2).
Marks et al., 1991, "By-passing immunization: Human antibodies from V-gene libraries displayed on phage," *J Mol Biol* 222:581-97.

(56) References Cited

OTHER PUBLICATIONS

Massarotti et al., 2002, Treatment Patterns in Early-Onset Rheumatoid Arthritis (RA): Results from the Sonora Study, *Ann Rheum Dis* 61(Suppl I):S93.
Medynski, 1994, "Phage Display: All Dressed Up and Ready to Role," *Bio/Technology* 12:1134-1136.
Multidose Pharmacokinetics Website Calculator, p. 1-7 (http://home.fuse.net/clymer/graphs/pkplot.html, accessed on May 30, 2013).
Munro & Capell, 1997, "Prevalence of Low Body Mass in Rheumatoid Arthritis: Association with the Acute Phase Response," *Ann Rheum Dis* 56(5):326-329.
Mutschler, 1981, "Arzneimittelwirkungen," Wissenschaftliche Verlagsgesellschaft mbH, 4$^{th}$ Ed. Chapter 2.6.5 p. 40-41.
Nancey et al., 2008, "Serum interleukin-6, Soluble interleukin-6 receptor and Crohn's disease activity," *Dig Dis Sci* 53:242-247.
National Institutes of Health definition of the term "dose" (nlm.nih.gov/medlineplus/mplusdictionary.html, accessed on Nov. 23, 2009), p. 1.
Nesbitt et al., 2007, "Mechanism of action of certolizumab pegol (CDP870): In vitro comparison with other anti-tumor necrosis factor α agents," *Inflamm Bowel Dis* 13(11):1323-1332.
Nilsson, 1995, "Antibody engineering," *Current Opinion in Structural Biology* 5:450-456.
Office Action cited during prosecution of U.S. Appl. No. 10/622,932, dated Apr. 16, 2010 (Inventor: Subhashis Bonerjee), pp. 1-17.
Office Action cited during prosecution of U.S. Appl. No. 11/435,844, dated Sep. 20, 2010 (Inventor: Rebecca S. Hoffman), pp. 1-18.
Office Action cited during prosecution of U.S. Appl. No. 10/422,287, dated Sep. 8, 2011, (Inventor: Steven Fischkoff), pp. 1-9.
Ogilvie et al., 2001, "Treatment of psoriatic arthritis with antitumour necrosis factor-a antibody clears skin lesions of psoriasis resistant to treatment with methotrexate," *British Journal of Dermatology* 144: 587-589.
Opposition of Amgen Inc. to EP 1 406 656 (Aug. 29, 2013), pp. 1-26.
Opposition of Pfizer Inc. to EP 1 406 656 (Sep. 26, 2013), pp. 1-17.
Opposition of AET BioTechnologie GmbH to EP 1 406 656 (Oct. 3, 2013), pp. 1-26.
Opposition of Kilburn & Strode LLP to EP 1 406 656 (Oct. 7, 2013), pp. 1-29.
Opposition of Gedeon Richter Pharma GmbH to EP 1 406 656 (Oct. 7, 2013), pp. 1-17.
Opposition of Strawman Limited to EP 1 406 656 (Oct. 7, 2013), pp. 1-13.
Opposition of Generics [UK] Limited (trading as Mylan) to EP 1 406 656 (Oct. 7, 2013), pp. 1-40.
Opposition of Teva Pharmaceutical Industries Ltd. to EP 1 406 656 (Oct. 8, 2013), pp. 1-15.
Opposition of George Schlich to EP 1 406 656 (Oct. 8, 2013), pp. 1-37.
Opposition of Zwicker, Schnappauf & Partner to EP 1 406 656 (Oct. 8, 2013), pp. 1-48.
Opposition of Wolfgang Weiss to EP 1 406 656 (Oct. 8, 2013), pp. 1-46.
Opposition of Markus Breuer to EP 1 406 656 (Oct. 8, 2013), pp. 1-26.
Opposition of Christian Apelt to EP 1 406 656 (Oct. 9, 2013), pp. 1-24.
Opposition of William E. Bird to EP 1 406 656 (Oct. 9, 2013), pp. 1-52.
Opposition of Hoffman-Eitle to EP 1 406 656 (Oct. 9, 2013), pp. 1-82.
Osborn et al., 2005, "From rodent reagents to human therapeutics using antibody guided selection," *Methods* 36:61-68.
Paulus et al., 2000, "Relative Contributions of the Components of the American College of Rheumatology 20% Criteria for Improvement to Responder Status in Patients with Early Seropositive Rheumatoid Arthritis," *Arthritis Rheum* 43(12):2743-5270.
Pincus et al., 1999, "Combination Therapy with Multiple Disease-Modifying Antirheumatic Drugs in Rheumatoid Arthritis: A Preventive Strategy," *Ann Intern Med* 131:768-774.

PK Solutions 2.0 Website, pp. 1-12 (http://www.summitpk.com/pksolutions/pksolutions.htm, accessed on Dec. 12, 2000).
PR Newswire, 2001, "Abbott Laboratories' D2E7—the next generation anti-TNF—shows promise in rheumatoid arthritis patients," Abbott Press Release, pp. 1-2.
PR Newswire—FirstCall "Abbott Laboratories' HUMIRA® Adalimumab Marks Successful First Year Treating Patients with Rheumatoid Arthritis," Dec. 30, 2003, pp. 1-4.
Prescribing Information for Humira (adalim umab) Injection, Solution for Subcutaneous use Initial U.S. Approval: 2002 (Updated Mar. 2009), pp. 1-53.
Prescribing information for REMICADErm (infliximab), © Centocor, Inc. 2000, Malvern, PA, USA, Revised Dec. 1, 2000, pp. 14-31.
Present et al., 1999, "Infliximab for the treatment of fistulas in patients with Crohn's disease," *N Engl J Med* 340:1398-1405.
Queen et al., 1989, "A humanized antibody that binds to the interleukin 2 receptor," *Proc Natl Acad Sc USA* 86:10029-10033.
Rajpal et al., 2005, "A General Method for Greatly Improving the Affinity of Antibodies by Using Combinatorial Libraries," *Proc Natl Acad Sc USA* 102(24):8466-8471.
Rau et al., 1998, "Long-term Efficacy and Tolerability of Multiple I.V. Doses of the Fully Human Anti-TNF-Antibody D2E7 in Patients with Arthritis," *Arthritis Rheum* 41(Suppl 9):S55 (abstract 137).
Rau et al., 1999, "Effective Combination of the Fully Human Anti-TNF Antibody D2E7 and Methotrexate in Active Rheumatoid Arthritis," *Ann Rheum Dis* 58(Suppl):217 (abstract 907).
Rau et al., 1999, "Erfahrungen mit D2E7" [Experiments with D2E7], *Z Rheumatol* 58(Suppl 1):I21 (abstract S51).
Rau et al., 1999, "Kombinationstherapie mit dem humanen Anti-TNF-Antikorper D2E7 und Merhotrexat bei aktiver chronischer Polyarthritis," *Z Rheumatol* 58(1):i35 (abstract F20).
Rau et al., 1999, "Long-Term Treatment with the Fully Human Anti-TNF-Antibody D2E7 Slows Radio-Graphic Disease Progression in Rheumatoid Arthritis," *Arthritis Rheum* 42(Suppl 9):S400 (abstract 1978).
Rau et al., 1999, "Wirkung und Vertraglichkeit wiederholter intravenoser Gaben des humanen anti-TNF Antikorpers D2E7 bei Patienten mit chronischer Polyarthritis," *Z Rheumatol* 58(Suppl 1):1/41, p. 12.
Rau et al., 2000, "Erfahrungen Mit D2E7," *Aktuel Rheumatol* 25(3):83-88.
Rau, R. et al., 2002, "2.5-Year Treatment Results With Adalimumab (D2E7), the First Fully Human Anti-Tnf Monoclonal Antibody, in Combination With Methotrexate in Active Rheumatoid Arthritis," *Ann Rheum Dis* 61(Suppl 1):S55.
Rau, 2002, "Adalimumab (a fully human anti-tumor necrosis factor α monoclonal antibody) in the treatment of active rheumatoid arthritis: the initial results of five trials," *Ann Rheum Dis* 51(Suppl II):ii70-ii73.
Rau et al., 2002, "Treatment with Adalimumab (D2E7), the Fully Human Anti-TNF Monoclonal Antibody, Slows Radiographic Disease Progression in Rheumatoid Arthritis: Results of a 12-Month Study," *J Clin Rheum* 8(Suppl):S78 (abstract 116).
Reinhart et al., 1996, "Assessment of the safety and efficacy of the monoclonal anti-tumor necrosis factor antibody-fragment, MAK 195F, in patients with sepsis and septic shock: A multicenter, randomized, placebo-controlled, dose-ranging study," *Crit Care Med* 24(5):733-742.
Reinisch et al., 1999, "Clinical relevance of serum interleukin-6 in Crohn's disease: S ingle point measurements, therapy monitoring, and prediction of clinical relapse," *Am J Gastroenterol* 94: 2156-2164.
Revicki et al., 2002, "Treatment with A dalimumab (D2E7), a Fully Human Anti-TNF Monoclonal Antibody, Improves Physical Function, Vitality, and Mental Health While Reducing Bodily Pain in Patients with Active Rheumatoid Arthritis (RA)," *Arthritis Rhe um* 46(Suppl 9):S537.
Ricart et al., 2001,"Infliximab for Crohn's disease in clinical practice at the Mayo Clinic: the first 100 patients," *Am J Gastroenterol*, Elsevier Science Inc., US, 96(3)722-729.

(56) References Cited

OTHER PUBLICATIONS

Riechmann et al., 1993, "Phage Display and Selection of a Site-Directed Randomized Single-Chain Antibody Fv Fragment for Its Affinity Improvement," *Biochemistry* 32:8848-8855.
Rinehart-Kim et al., 2000, "Alterations in the gene expression profile of MCF-7 breast tumor cells in response to c-Jun," *Int J Cancer* 88(2):180-190.
Rodgers & Miller, 2012, "Cytokine Control of Inflammation and Repair in Pathology of Multiple Sclerosis," *Yale J Biol Med* 85(4):447-468.
Rowland and Tozer, Clinical Pharmacokinetics: concepts and applications, 3$^{rd}$ d Ed., Lippincott Williams and Wilkins, 1995, pp. 83-105.
Rudikoff et al., 1982, "Single amino acid substitution altering antigen-binding specificity, " *PNAS* 79:1979-1983.
Salfeld et al., 1998, "Generation of Fully Human Anti-TNF Antibody D2E7," *Arthritis Rheum* 41(Suppl 9):S57.
Sandborn et al., 1999, "Antitumor Necrosis Factor Therapy for Inflammatory Bowel Disease: A Review of Agents, Pharmacology, Clinical Results, and Safety," *Inflamm Bowel Dis* 5(2):119-133.
Sandborn et al., 2001, "An Engineered Human Antibody to TNF (CDP571) for Active Crohn's Disease: A Randomized Double-blind Placebo-Controlled Trial," *Gastroenterology* 120(6):1330-1338.
Santora et al., 1999, "Characterization of Recombinant Human Monoclonal Tissue Necrosis Factor-a Antibody Using Cation-Exchange HPLC and Capillary Isoelectric Focusing," *Analytical Biochemistry* 275:98-108.
Santora et al., 2001, "Characterization of Noncovalent Complexes of Recombinant Human Monoclonal Antibody and Antigen Using Carbon Exchange, Size Exclusion Chromatography, and BIAcore," *Analytical Biochemistry* 299(2):119-129.
Schattenkirchner et al., 1998, "Efficacy and Tolerability of Weekly Subcutaneous Injections of the Fully Human Anti-TNF-Antibody D2E7 in Patients with Rheum atoid Arthritis—Results of a Phase I Study," *Arthritis Rheum* 41(Suppl 9):S57 (abstract 149).
Schattenkirchner et al., 1999, "Phase-1-Studie zur Wirksamkeit und Verträglichkeit wöchentli cher subcutaner Injektion des humanen Anti-TNF Antikörpers D2E7 bei cP," *Z Rheumatol* 58(Suppl 1):I42 (abstract p. 14).
Schattenkirchner et al., 2000, "Long-term Use of the Fully Human Anti-TNF Antibody D2E7 in Combination with Methotrexate in Active Rheumatoid Arthritis," *Arthritis Rheum* 43(Suppl 9):S228 (abstract 968).
Schattenkirchner et al., 2001, "Long-term Use of the Fully Human Anti-TNF Antibody Adalim umab (D2E7) in Dmard-refractory Rheumatoid Arthritis," Presented at: *The Annual Meeting of the European League Against Rheumatism (EULAR)*, Prague, Czech Republic, Jun. 2001, pp. 1-3.
Schiff et al., 2002, "A Randomized, Controlled, Safety Trial of Adalim umab (D2E7), a Fully Human Anti-TNF Monoclonal Antibody, Given to RA Patients in Combination with Standard Rheumatologic Care: The STAR (Safety Trial of Adalimumab in Rheumatoid Arthritis) Trial," *Ann Rheum Dis* 61(Suppl 1):S169.
Scott, 2013, Declaration (I) in opposition proceedings to EP 1 406 656, pp. 1-69.
Scott, 2013, Declaration (II) in opposition proceedings to EP 1 406 656, pp. 1-10.
Shargel et al., 1999, Applied Biopharmaceutics and Pharmacokinetics, "Rates and Orders of Reactions," 4$^{th}$ Ed., Appleton and Lange, 21-25.
Shargel et al., 1999, Applied Biopharmaceutics and Pharmacokinetics, "Rates and Orders of Reactions," 4$^{th}$ Ed., Appleton and Lange, 399-404.
Shealy et al., 2010, "Characterization of golimumab, a human monoclonal antibody specific for human tumor necrosis factor α," mAbs 2(4):428-439.
Shoenfeld et al., 2008, "Diagnostic Criteria in Autoimmune Disease" Humana Press, Preface and Table of Contents (17 pages).
Sibilia, 2002, "Combinaison de traitements de fond dans la polyarthrite rhumatoIde," *Ann Med Interne* 153(1):41-52.

Simianer et al., 2000, "One year treatment results of the fully human anti-TNF antibody D2E7 in combination with methotrexate in active rheumatoid arthritis," Presented at *European League Against Rheumatism—Annual Congress* (abstract POS-370) , pp. 1-2.
Sorbera et al., 2001, "A dalimumab," *Drugs of the Future* 26(7):639-646.
Sowerbutt, 2001, "ACR: Adalimumab (D2E7) in patients with active RA on methotrexate (MTX)," DG News, p. 1.
Stockinger (Protein Reviews on the Web, http://mpr.nci.nih.gov/prow/guide/1397527348_g.htm, last modified on Oct. 14, 1999).
Strand et al., 2002, "Treatment with Adalimumab (D2E7), a Fully Human Anti-TNF Monoclonal Antibody, Improves Physical Function and Health Related Quality of Life (HRQOL) in Patients with Active Rheumatoid Arthritis (RA)," *Ann Rheum Dis* 61(Suppl I):S175.
Stroebele et al., 2010, "Identifying the energy gap in the German population using results from representative national health surveys (1985-2002)," *Public Health Nutr* 14(1)44-48.
Taber's Cyclopedic Medical Dictionary, 1977, Clayton L. Thomas (ed.) 13$^{th}$ Ed., F.A. Davis Co., "subcutaneous" pp. S-118-S-119.
Taber's Cyclopedic Medical Dictionary, 1993, Clayton L. Thomas (ed.) 17$^{th}$ Ed., F.A. Davis Co. , "intravenous injection" pp. 1013-1014.
Tamura et al., 2000, "Structural correlates of an anticarcinoma antibody: identification of specificity-determining residues (SDRs) and development of a minimally immunogenic antibody variant by retention of SDRs only," *J Immunol* 164:1432-1441.
Taylor et al., 2001, "Anti-Tumor Necrosis Factor Therapies," *Curr Op Rheumatol* 13:164-169.
Thompson et al., 1996, "Affinity maturation of a high-affinity human monoclonal antibody against the third hypervariable loop of human immunodeficiency virus: use of phage display to improve affinity and broaden strain reactivity," *J Mol Biol* 256:77-88.
Tomlinson et al., 1992, "The repertoire of human germline VH sequences reveals about fifty groups of VH segments with different hypervariable loops," *J Mol Biol* 227:776-798.
Tomlinson et al., 1995,"The structural repertoire of the human Vk domain," *The EMBO J* 14(18):4628-4638.
Tracey et al., 1994, "Tumor necrosis factor: A pleiotropic cytokine and therapeutic target," *Annu Rev Med* 45:491-503.
Trade register HR B 4800 (as submitted to EPO on Oct. 8, 2013) , pp. 1-4.
Trade register HR B 5169 (as submitted to EPO on Oct. 8, 2013) , pp. 1-12.
Tripathi, 2003, "Essentials of Medical Pharmacology," *Jaypee Brothers Medical Publishers (P) Ltd.*, 5$^{th}$ Ed., Ch. 3, pp. 51-56.
Vadjos et al., 2002, "Comprehensive Functional Maps of the Antigen-binding Site of an Anti-ErbB2 Antibody Obtained with Shotgun Scanning Mutagenesis," *J Mol Biol* 320(2):415-428.
Van Assche et al., 2000, "Anti-TNF Agents in Crohn's Disease," *Expert Opinion on Investigational Drugs* 9(1):103-111.
van de Putte et al., 1998, "A single dose placebo-controlled phase I study of the fully human anti-TNF antibody D2E7 in patients with Rheumatoid Arthritis," *Arthritis Rheum* 41(Suppl 9):S57 (abstract 148).
van de Putte et al., 1999, "Efficacy of the Fully Human Anti-TNF Antibody D2E7 in Rheumatoid Arthritis," *Arthritis Rheum* 42(Suppl 9):S400 (abstract 1977).
van de Putte et al., 1999, "Eine placebo-kontrollierte Phase 1-Studie des humanen Anti-TNF-Antikörpers D2E7 bei Patienten mit aktiver chronischer Polyarthritis," *Z Rheumatol* 58(1):I34 (abstract F19).
van de Putte et al., 2000, "One Year Efficacy Results of the Fully Human Anti-TNF Antibody D2E7 in Rheumatoid Arthritis," *Arthritis Rheum* 42(9):S269 (abstract 1218).
van de Putte et al., 2000, "Six-month efficacy of the fully human anti-TNF antibody D2E7 in rheumatoid arthritis," *Ann Rheum Dis* 59 (Suppl 1) (abstract 056).
van de Putte et al., 2002, "Adalim umab (D2E7), the Fully Human Anti-TNF Monoclonal Antibody, in the Treatment of Patients with Rheumatoid Arthritis Who Failed Previous DMARD Therapy: Efficacy and Safety Results from a 6-Month Phase III Study," *J Clin Rheumatol* 8(Suppl 3):S89.

(56) References Cited

OTHER PUBLICATIONS van de Putte et al., 2002, "Efficacy and Safety of Adalimumab (D2E7), the First Fully Human Anti-TNF Monoclonal Antibody, in Patients with Rheumatoid Arthritis Who Failed Previous DMARD Therapy: 6-Month Results from a Phase III Study," *Ann Rheum Dis* 61(Suppl 1):S168.

van de Putte et al., 2002, "Adalim umab (D2E7) Monotherapy in the Treatment of Patients with Severely Active Rheumatoid Arthritis (RA)," *Arthritis Rheum* 46(Suppl 9):S171.

van de Putte et al., 2003, "Efficacy and safety of the fully human anti-tumor necrosis factor α monoclonal antibody adalimumab (D2E7) in DMARD refractory patients with rheumatoid arthritis: a 12 week, phase II study," *Ann Rheum Dis* 62(12):1168-1177.

van de Putte, 2003, "Adalim umab." In: INFa-Inhibition in the Treat ment of Rheumatoid Arthritis, Moreland and Emery (eds.), Martin Dunitz, London, pp. 71-93.

van de Putte et al., 2004, "Efficacy and Safety of Adalimumab as Monotheraphy in Patients with Rheumatoid Arthritis for whom Previous Disease Modifying Antirheumatic Drug Treatment Has Failed," *Ann Rheum Dis* 63:508-516.

van der Poll et al., 1995, "Effect of postponed treatment with an anti-tum our necrosis factor (TNF) F(ab')2 fragment on endotoxin-induced cytokine and neutrophil responses in chimpanzees," *Clin Exp Immunol* 100:21-25.

van Riel et al., 2001, "How does one assess early rheumatoid arthritis in clinical practice?" *Best Practice & Research Clinical Rheumatology* 15(1):67-76.

van Riel et al., 2002, "Long-Term Treatm ent with Adalimumab (D2E7) Using Background Meth otrexate in Active Rheumatoid Arthritis: Results of a 3 Year Study," *Arthritis R heum* 46 (Suppl 9):S534.

Vaughan et al., 1998, "Human antibodies by design," *Nature Biotechnology* 16:535-539.

Velagapudi et al., 2002, "Pharmacokinetics of Adalim umab (D2E7), a Fully Human Anti-TNF-α Monoclonal Antibody, Following a Single Intravenous Injection in Rheumatoid Arthritis Patients Treated with Meth otrexate," *Arthritis Rheum* 46(Suppl 9):S133.

Wailoo et al., 2006, "Modeling the cost effectiveness of Etanercept, Adalim umab and A nakinra Compared to Infliximab in the Treatment of Patients with Rhe umatoid Arthritis in the Medicare Program," Agency for healthcare research a nd quality, Final Report Oct. 12, 2006, pp. 1-74.

Ward et al., 1989, "Binding activities of a repertoire of single immunoglobulin variable domains secreted from *Escherichia coli*," *Nature* 341:544-546.

Weinblatt et al., 2003, "Adalimumab, a fully human anti-tumor necrosis factor α monoclonal antib ody, for the treatment of Rheumatoid Arthritis in patients taking concomitant methotrexate," *Arthritis Rheum* 48(1):35-45.

Weisman et al., 2000, "A Dose Escalation Study Designed to Demonstrate the Safety, Tolerability and Efficacy of the Fully Human Anti-TNF Antibody, D2E7, Given in Combination with Methotrexate (MTX) in Patients with Active RA," *Arthritis Rheum* 43(Suppl 9):S391 (abstract 1948).

Weisman, 2013, Declaration in opposition proceedings to EP 1 406 656, pp. 1-11.

Wellborne et al., 2002, "Adalim umab (D2E7), a Fully Human Anti-TNF-α Monoclonal Antibody, Improved Health-Related Quality of Life in Patients with Active Rheumatoid Arthritis Despite Concomitant Methotrexate Therapy," *Arthritis Rheum* 46(Suppl 9):S518.

Wells et al., 2002, "Incidence of Injection-Site Reactions Associated with Adalim umab (D2E7) Give Subcutaneously for at Least 6 Months: A Retrospective Analysis of 4 Phase II/III Clinical Trials," *Arthritis Rheum* 46(Suppl 9):S171.

Wiendl et al., 2000, "Multiple sclerosis. Current review of failed and discontinued clinical trials of drug treatment," Der Nervenarzt, LNKD-PubMed: 10996910, 71(8):597-610.

Wildy & Wasko, 2001, "Current Concepts Regarding Pharmacologic Treatment of Rheumatoid and Osteoarthritis," *Hand Clinics* 17(2):321-338.

Winter et al., 1993, "Humanized antibodies," *Immuno Today* 14(6):243-246.

Winter et al., 1994, "Making Antibodies by Phage Display Technology," *Ann Ren Immunol* 12:433-445.

Zia-Amirhosseini et al., 1999, "Pharmacokinetics and pharmacodynamics of SB-240563, a humanized monoclonal antibody directed to human interleukin-5, in monkeys," *J Pharmacol Exp Ther* 291(3):1060-1067.

Rowland & Unadkat, 1981, Acceptable Sampling Times at Plateau for Drug Analysis, *Br. J. Clin. Phar mac.* 12:687-689.

\* cited by examiner

Study DE007
Dosing every week

Study DE009
Dosing every other week

SF-36 SCALE

SEQUENCE LISTING

<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: mutated human antibody
<220> FEATURE:
<223> OTHER INFORMATION: mutated human antibody

<400> SEQUENCE: 1

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
```

```
                 20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: mutated human antibody

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: mutated human antibody
<220> FEATURE:
<221> NAME/KEY: VARIANT
<222> LOCATION: (9)
<223> OTHER INFORMATION: Xaa = Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: mutated human antibody
<220> FEATURE:
<221> NAME/KEY: VARIANT
<222> LOCATION: (12)
<223> OTHER INFORMATION: Xaa = Tyr or Asn
```

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: mutated human antibody

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: mutated human antibody

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: mutated human antibody

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: mutated human antibody

<400> SEQUENCE: 8

Asp Tyr Ala Met His
1               5

<210> SEQ ID NO 9
<211> LENGTH: 107
<212> TYPE: PRT
<213> ORGANISM: Artificial Sequence
<220> FEATURE:
<223> OTHER INFORMATION: mutated human antibody

<400> SEQUENCE: 9

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: mutated human antibody

<400> SEQUENCE: 10

Gln Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
            35                  40                  45

Ser Ala Ile Thr Trp Asn Ser Gly His Ile Asp Tyr Ala Asp Ser Val
            50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: mutated human antibody

<400> SEQUENCE: 11

Gln Lys Tyr Asn Ser Ala Pro Tyr Ala
1               5

<210> SEQ ID NO 12
<211> LENGTH: 9
<212> TYPE: PRT
<213> ORGANISM: Artificial Sequence
<220> FEATURE:
<223> OTHER INFORMATION: mutated human antibody

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial Sequence
<220> FEATURE:
<223> OTHER INFORMATION: mutated human antibody

<400> SEQUENCE: 13

Gln Lys Tyr Gln Arg Ala Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: mutated human antibody

<400> SEQUENCE: 14

Gln Lys Tyr Ser Ser Ala Pro Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: mutated human antibody

<400> SEQUENCE: 15

Gln Lys Tyr Asn Ser Ala Pro Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: mutated human antibody

<400> SEQUENCE: 16

Gln Lys Tyr Asn Arg Ala Pro Tyr Thr
1               5

<210> SEQ ID NO 17
<211> LENGTH: 9
<212> TYPE: PRT
<213> ORGANISM: Artificial Sequence
<220> FEATURE:
<223> OTHER INFORMATION: mutated human antibody

<400> SEQUENCE: 17

Gln Lys Tyr Asn Ser Ala Pro Tyr Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: mutated human antibody

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial Sequence
<220> FEATURE:
<223> OTHER INFORMATION: mutated human antibody

```
<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: mutated human antibody

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial Sequence
<220> FEATURE:
<223> OTHER INFORMATION: mutated human antibody

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial Sequence
<220> FEATURE:
<223> OTHER INFORMATION: mutated human antibody

<400> SEQUENCE: 22

Gln Gln Tyr Asn Ser Ala Pro Asp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: mutated human antibody

<400> SEQUENCE: 23

Gln Lys Tyr Asn Ser Asp Pro Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: mutated human antibody

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial Sequence
<220> FEATURE:
<223> OTHER INFORMATION: mutated human antibody

<400> SEQUENCE: 25
```

```
Gln Lys Tyr Asn Arg Pro Pro Tyr Thr
 1               5

<210> SEQ ID NO 26
<211> LENGTH: 9
<212> TYPE: PRT
<213> ORGANISM: Artificial Sequence
<220> FEATURE:
<223> OTHER INFORMATION: mutated human antibody

<400> SEQUENCE: 26

Gln Arg Tyr Asn Arg Ala Pro Tyr Ala
 1               5

<210> SEQ ID NO 27
<211> LENGTH: 12
<212> TYPE: PRT
<213> ORGANISM: Artificial Sequence
<220> FEATURE:
<223> OTHER INFORMATION: mutated human antibody

<400> SEQUENCE: 27

Ala Ser Tyr Leu Ser Thr Ser Ser Ser Leu Asp Asn
 1               5                   10

<210> SEQ ID NO 28
<211> LENGTH: 12
<212> TYPE: PRT
<213> ORGANISM: Artificial Sequence
<220> FEATURE:
<223> OTHER INFORMATION: mutated human antibody

<400> SEQUENCE: 28

Ala Ser Tyr Leu Ser Thr Ser Ser Ser Leu Asp Lys
 1               5                   10

<210> SEQ ID NO 29
<211> LENGTH: 12
<212> TYPE: PRT
<213> ORGANISM: Artificial Sequence
<220> FEATURE:
<223> OTHER INFORMATION: mutated human antibody

<400> SEQUENCE: 29

Ala Ser Tyr Leu Ser Thr Ser Ser Ser Leu Asp Tyr
 1               5                   10

<210> SEQ ID NO 30
<211> LENGTH: 12
<212> TYPE: PRT
<213> ORGANISM: Artificial Sequence
<220> FEATURE:
<223> OTHER INFORMATION: mutated human antibody

<400> SEQUENCE: 30

Ala Ser Tyr Leu Ser Thr Ser Ser Ser Leu Asp Asp
 1               5                   10

<210> SEQ ID NO 31
<211> LENGTH: 12
<212> TYPE: PRT
<213> ORGANISM: Artificial Sequence
<220> FEATURE:
<223> OTHER INFORMATION: mutated human antibody

<400> SEQUENCE: 31
```

```
Ala Ser Tyr Leu Ser Thr Ser Phe Ser Leu Asp Tyr
 1               5                  10
```

<210> SEQ ID NO 32
<211> LENGTH: 12
<212> TYPE: PRT
<213> ORGANISM: Artificial Sequence
<220> FEATURE:
<223> OTHER INFORMATION: mutated human antibody

<400> SEQUENCE: 32

```
Ala Ser Tyr Leu Ser Thr Ser Ser Ser Leu His Tyr
 1               5                  10
```

<210> SEQ ID NO 33
<211> LENGTH: 12
<212> TYPE: PRT
<213> ORGANISM: Artificial Sequence
<220> FEATURE:
<223> OTHER INFORMATION: mutated human antibody

<400> SEQUENCE: 33

```
Ala Ser Phe Leu Ser Thr Ser Ser Ser Leu Glu Tyr
 1               5                  10
```

<210> SEQ ID NO 34
<211> LENGTH: 12
<212> TYPE: PRT
<213> ORGANISM: Artificial Sequence
<220> FEATURE:
<223> OTHER INFORMATION: mutated human antibody

<400> SEQUENCE: 34

```
Ala Ser Tyr Leu Ser Thr Ala Ser Ser Leu Glu Tyr
 1               5                  10
```

<210> SEQ ID NO 35
<211> LENGTH: 12
<212> TYPE: PRT
<213> ORGANISM: Artificial Sequence
<220> FEATURE:
<223> OTHER INFORMATION: mutated human antibody

<400> SEQUENCE: 35

```
Val Ser Tyr Leu Ser Thr Ala Ser Ser Leu Asp Asn
 1               5                  10
```

<210> SEQ ID NO 36
<211> LENGTH: 321
<212> TYPE: DNA
<213> ORGANISM: Artificial Sequence
<220> FEATURE:
<223> OTHER INFORMATION: mutated human antibody

<400> SEQUENCE: 36

```
gacatccaga tgacccagtc tccatcctcc ctgtctgcat ctgtagggga cagagtcacc    60
atcacttgtc gggcaagtca gggcatcaga aattacttag cctggtatca gcaaaaacca   120
gggaaagccc ctaagctcct gatctatgct gcatccactt tgcaatcagg ggtcccatct   180
cggttcagtg gcagtggatc tgggacagat ttcactctca ccatcagcag cctacagcct   240
gaagatgttg caacttatta ctgtcaaagg tataaccgtg caccgtatac ttttggccag   300
gggaccaagg tggaaatcaa a                                             321
```

<210> SEQ ID NO 37

```
<211> LENGTH: 363
<212> TYPE: DNA
<213> ORGANISM: Artificial Sequence
<220> FEATURE:
<223> OTHER INFORMATION: mutated human antibody

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tggagggccg attcaccatc tccagagaca acgccaagaa ctccctgtat     240
ctgcaaatga acagtctgag agctgaggat acggccgtat attactgtgc gaaagtctcg     300
taccttagca ccgcgtcctc ccttgactat tggggccaag gtaccctggt caccgtctcg     360
agt                                                                   363
```

METHODS OF ADMINISTERING ANTI-TNFα ANTIBODIES

CROSS-REFERENCE TO RELATED APPLICATIONS

The present application is a continuation of U.S. application Ser. No. 10/163,657, filed on Jun. 5, 2002, which claims the benefit of U.S. Provisional Application No. 60/296,961, filed Jun. 8, 2001. Each of these applications is hereby incorporated by reference in its entirety.

BACKGROUND OF THE INVENTION

Tumor necrosis factor α (TNFα) is a cytokine produced by numerous cell types, including monocytes and macrophages, that was originally identified based on its capacity to induce the necrosis of certain mouse tumors (see e.g., Old, L. (1985) *Science* 230:630-632). Subsequently, a factor termed cachectin, associated with cachexia, was shown to be the same molecule as TNFα. TNFα has been implicated in mediating shock (see e.g., Beutler, B. and Cerami, A. (1988) *Annu. Rev. Biochem.* 57:505-518; Beutler, B. and Cerami, A. (1989) *Annu. Rev. Immunol.* 7:625-655). Furthermore, TNFα has been implicated in the pathophysiology of a variety of other human diseases and disorders, including sepsis, infections, autoimmune diseases, transplant rejection and graft-versus-host disease (see e.g., Vasilli, P. (1992) *Annu. Rev. Immunol.* 10:411-452; Tracey, K. J. and Cerami, A. (1994) *Annu. Rev. Med.* 45:491-503).

Because of the harmful role of human TNFα (hTNFα) in a variety of human disorders, therapeutic strategies have been designed to inhibit or counteract hTNFα activity. In particular, antibodies that bind to, and neutralize, hTNFα have been sought as a means to inhibit hTNFα activity. Some of the earliest of such antibodies were mouse monoclonal antibodies (mAbs), secreted by hybridomas prepared from lymphocytes of mice immunized with hTNFα (see e.g., Hahn T; et al., (1985) *Proc Natl Acad Sci USA* 82: 3814-3818; Liang, C-M., et al. (1986) *Biochem. Biophys. Res. Commun.* 137:847-854; Hirai, M., et al. (1987) *J. Immunol. Methods* 96:57-62; Fendly, B. M., et al. (1987) *Hybridoma* 6:359-370; Möller, A., et al. (1990) *Cytokine* 2:162-169; U.S. Pat. No. 5,231,024 to Moeller et al.; European Patent Publication No, 186 833 B1 by Wallach, D.; European Patent Application Publication No. 218 868 A1 by Old et al.; European Patent Publication No. 260 610 B1 by Moeller, A., et al.). While these mouse anti-hTNFα antibodies often displayed high affinity for hTNFα (e.g., Kd≤$10^{-9}$M) and were able to neutralize hTNFα activity, their use in vivo may be limited by problems associated with administration of mouse antibodies to humans, such as short serum half life, an inability to trigger certain human effector functions and elicitation of an unwanted immune response against the mouse antibody in a human (the "human anti-mouse antibody" (HAMA) reaction).

In an attempt to overcome the problems associated with use of fully-murine antibodies in humans, murine anti-hTNFα antibodies have been genetically engineered to be more "human-like." For example, chimeric antibodies, in which the variable regions of the antibody chains are murine-derived and the constant regions of the antibody chains are Continuation of application Ser. No. 10/163,657-human-derived, have been prepared (Knight, D. M, et al. (1993) *Mol. Immunol.* 30:1443-1453; PCT Publication No. WO 92/16553 by Daddona, P. E., et al.). Additionally, humanized antibodies, in which the hypervariable domains of the antibody variable regions are murine-derived but the remainder of the variable regions and the antibody constant regions are human-derived, have also been prepared (PCT Publication No. WO 92/11383 by Adair, J. R., et al.). However, because these chimeric and humanized antibodies still retain some murine sequences, they still may elicit an unwanted immune reaction, the human anti-chimeric antibody (HACA) reaction, especially when administered for prolonged periods, e.g., for chronic indications, such as rheumatoid arthritis (see e.g., Elliott, M. J., et al. (1994) *Lancet* 344:1125-1127; Elliot, M. J., et al. (1994) *Lancet* 344:1105-1110).

A preferred hTNFα inhibitory agent to murine mAbs or derivatives thereof (e.g., chimeric or humanized antibodies) would be an entirely human anti-hTNFα antibody, since such an agent should not elicit the HAMA reaction, even if used for prolonged periods. Human monoclonal autoantibodies against hTNFα have been prepared using human hybridoma techniques (Boyle, P., et al. (1993) *Cell. Immunol.* 152:556-568; Boyle, P., et al. (1993) *Cell. Immunol.* 152:569-581; European Patent Application Publication No. 614 984 A2 by Boyle, et al.). However, these hybridoma-derived monoclonal autoantibodies were reported to have an affinity for hTNFα that was too low to calculate by conventional methods, were unable to bind soluble hTNFα and were unable to neutralize hTNFα-induced cytotoxicity (see Boyle, et al.; supra). Moreover, the success of the human hybridoma technique depends upon the natural presence in human peripheral blood of lymphocytes producing autoantibodies specific for hTNFα. Certain studies have detected serum autoantibodies against hTNFα in human subjects (Fomsgaard, A., et al. (1989) *Scand. J. Immunol.* 30:219-223; Bendtzen, K., et al. (1990) *Prog. Leukocyte Biol.* 10B:447-452), whereas others have not (Leusch, H-G., et al. (1991) *J. Immunol. Methods* 139:145-147).

Alternative to naturally-occurring human anti-hTNFα antibodies would be a recombinant hTNFα antibody. Recombinant human antibodies that bind hTNFα with relatively low affinity (i.e., $K_d$~$10^{-7}$M) and a fast off rate (i.e., $K_{off}$~$10^{-2}$ $sec^{-1}$) have been described (Griffiths, A. D., et al. (1993) *EMBO J.* 12:725-734). However, because of their relatively fast dissociation kinetics, these antibodies may not be suitable for therapeutic use. Additionally, a recombinant human anti-hTNFα has been described that does not neutralize hTNFα activity, but rather enhances binding of hTNFα to the surface of cells and enhances internalization of hTNFα (Lidbury, A., et al. (1994) *Biotechnol. Ther.* 5:27-45; PCT Publication No. WO 92/03145 by Aston, R. et al.)

Recombinant human antibodies that bind soluble hTNFα with high affinity and slow dissociation kinetics and that have the capacity to neutralize hTNFα activity, including hTNFα-induced cytotoxicity (in vitro and in vivo) and hTNFα-induced cell activation, have also been described (see U.S. Pat. No. 6,090,382). Typical protocols for administering antibodies are performed intravenously on a weekly basis. Weekly dosing with antibodies and/or any drug can be costly, cumbersome, and result in an increase in the number of side effects due to the frequency of administration. Intravenous administration also has limitations in that the administration is usually provided by someone with medical training.

SUMMARY OF THE INVENTION

The present invention provides methods for biweekly dosing regimens for the treatment of TNFα associated disorders, preferably via a subcutaneous route. Biweekly dosing has many advantages over weekly dosing including, but not limited to, a lower number of total injections, decreased number of injection site reactions (e.g., local pain and swelling), increased patient compliance (i.e., due to less frequent injections), and less cost to the patient as well as the health care provider. Subcutaneous dosing is advantageous because the patient may self-administer a therapeutic substance, e.g., a human TNFα antibody, which is convenient for both the patient and the health care provider.

This invention provides methods for treating disorders in which TNFα activity is detrimental. The methods include administering biweekly, subcutaneous injections of antibodies to a subject. The antibodies preferably are recombinant human antibodies that specifically bind to human TNFα. This invention further provides methods for treating disorders in which TNFα activity is detrimental. These methods include utilizing a combination therapy wherein human antibodies are administered to a subject with another therapeutic agent, such as one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751), preferably methotrexate. The antibodies are preferably recombinant human antibodies that specifically bind to human TNFα. The antibodies of the invention are characterized by binding to hTNFα with high affinity and slow dissociation kinetics and by neutralizing hTNFα activity, including hTNFα-induced cytotoxicity (in vitro and in vivo) and hTNFα-induced cellular activation. The antibodies can be full-length (e.g., an IgG1 or IgG4 antibody) or can comprise only an antigen-binding portion (e.g., a Fab, F(ab')$_2$, scFv fragment or single domain). The most preferred recombinant antibody of the invention, termed D2E7, has a light chain CDR3 domain comprising the amino acid sequence of SEQ ID NO: 3 and a heavy chain CDR3 domain comprising the amino acid sequence of SEQ ID NO: 4 (set forth in Appendix B). Preferably, the D2E7 antibody has a light chain variable region (LCVR) comprising the amino acid sequence of SEQ ID NO: 1 and a heavy chain variable region (HCVR) comprising the amino acid sequence of SEQ ID NO: 2. These antibodies are described in U.S. Pat. No. 6,090,382, incorporated in its entirety herein by reference.

In one embodiment, the invention provides methods of treating disorders in which TNFα activity is detrimental. These methods include inhibiting human TNFα activity by subcutaneous, biweekly administration of an anti-TNFα antibody such that the disorder is treated. The disorder can be, for example, sepsis, an autoimmune disease (e.g., rheumatoid arthritis, allergy, multiple sclerosis, autoimmune diabetes, autoimmune uveitis and nephrotic syndrome), an infectious disease, a malignancy, transplant rejection or graft-versus-host disease, a pulmonary disorder, a bone disorder, an intestinal disorder or a cardiac disorder.

In another embodiment, the invention provides methods of treating disorders in which TNFα activity is detrimental. These methods include inhibiting human TNFα activity by subcutaneous administration of an anti-TNFα antibody and methotrexate such that the disorder is treated. In one aspect, methotrexate is administered together with an anti-TNFα antibody. In another aspect, methotrexate is administered prior to the administration of an anti-TNFα antibody. In still another aspect, methotrexate is administered subsequent to the administration of an anti-TNFα antibody.

In a preferred embodiment, the anti-TNFα antibody used to treat disorders in which TNFα activity is detrimental is a human anti-TNFα antibody. Even more preferably, treatment occurs by the biweekly, subcutaneous administration of an isolated human antibody, or an antigen-binding portion thereof. The antibody or antigen-binding portion thereof preferably dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less. More preferably, the isolated human antibody, or antigen-binding portion thereof, dissociates from human TNFα with a $K_{off}$ of $5 \times 10^{-4}$ s$^{-1}$ or less, or even more preferably, with a $K_{off}$ of $1 \times 10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1 \times 10^{-8}$ M or less, even more preferably with an IC$_{50}$ of $1 \times 10^{-9}$ M or less and still more preferably with an IC$_{50}$ of $1 \times 10^{-10}$ M or less.

In another embodiment, the invention provides methods of treating disorders in which TNFα activity is detrimental by the biweekly, subcutaneous administration to the subject a human antibody, or antigen-binding portion thereof. The antibody or antigen-binding portion thereof preferably has the following characteristics:

a) dissociates from human TNFα with a $K_{off}$ of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ s$^{-1}$ or less. Still more preferably, the antibody, or antigen-binding portion thereof, dissociates from human TNFα with a $K_{off}$ of $1 \times 10^{-4}$ s$^{-1}$ or less.

In yet another embodiment, the invention provides methods of treating disorders in which TNFα activity is detrimental. These methods include a biweekly, subcutaneous administration to the subject a human antibody, or an antigen-binding portion thereof. The antibody or antigen-binding portion thereof preferably contains an LCVR having CDR3 domain comprising the amino acid sequence of SEQ ID NO: 3, or modified from SEQ ID NO: 3 by a single alanine substitution at position 1, 4, 5, 7 or 8, and with an HCVR having a CDR3 domain comprising the amino acid sequence of SEQ ID NO: 4, or modified from SEQ ID NO: 4 by a single alanine substitution at position 2, 3, 4, 5, 6, 8, 9, 10 or 11. More preferably, the LCVR further has a CDR2 domain comprising the amino acid sequence of SEQ ID NO: 5 and the HCVR further has a CDR2 domain comprising the amino acid sequence of SEQ ID NO: 6. Still more preferably, the LCVR further has CDR1 domain comprising the amino acid sequence of SEQ ID NO: 7 and the HCVR has a CDR1 domain comprising the amino acid sequence of SEQ ID NO: 8.

In still another embodiment, the invention provides methods of treating disorders in which TNFα activity is detrimental by subcutaneously administering to the subject, biweekly, an isolated human antibody, or an antigen binding portion thereof. The antibody or antigen-binding portion thereof preferably contains an LCVR comprising the amino acid sequence of SEQ ID NO: 1 and an HCVR comprising the amino acid sequence of SEQ ID NO: 2. In certain embodiments, the antibody has an IgG1 heavy chain constant region or an IgG4 heavy chain constant region. In yet other embodiments, the antibody is a Fab fragment, an F(ab')$_2$ fragment or a single chain Fv fragment.

In still other embodiments, the invention provides methods of treating disorders in which the administration of an anti-TNFα antibody is beneficial by subcutaneously administering to the subject, biweekly, one or more anti-TNFα antibodies, or antigen-binding portions thereof. The antibody or antigen-binding portion thereof preferably contains an LCVR having CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 or with an HCVR having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

Still another aspect of the invention pertains to kits containing a formulation comprising a pharmaceutical composition. The kits comprise an anti-TNFα antibody and a pharmaceutically acceptable carrier. The kits contain instructions for biweekly subcutaneous dosing of the pharmaceutical composition for the treatment of a disorder in which the administration of an anti-TNFα antibody is beneficial. In another aspect, the invention pertains to kits containing a formulation comprising a pharmaceutical composition, further comprising an anti-TNFα antibody, methotrexate, and a pharmaceutically acceptable carrier. The kits contain instructions for subcutaneous dosing of the pharmaceutical composition for the treatment of a disorder in which the administration of an anti-TNFα antibody is beneficial.

Still another aspect of the invention provides a preloaded syringe containing a pharmaceutical composition comprising an anti-TNFα antibody and a pharmaceutically acceptable carrier. In still another aspect, the invention provides a preloaded syringe containing a pharmaceutical composition comprising an anti-TNFα antibody, methotrexate, and a pharmaceutically acceptable carrier.

DETAILED DESCRIPTION OF THE INVENTION

Figure 1:
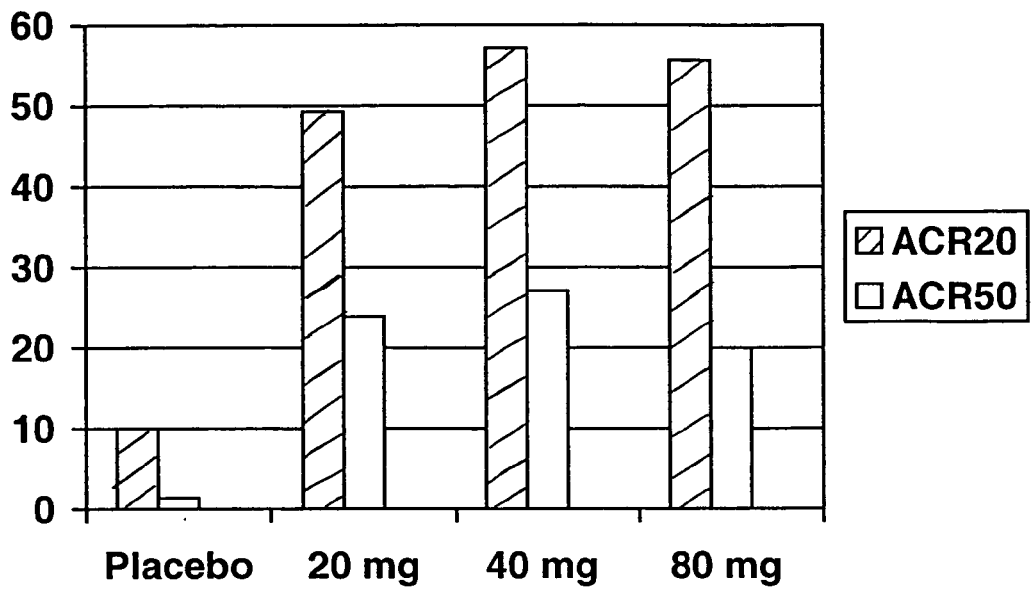
FIG. 1 depicts the American College of Rheumatology 20 (ACR20) and ACR50 responses for patients suffering from rheumatoid arthritis (RA) after subcutaneous dosing with the antibody D2E7 every week for a total of twelve weeks (top), or subcutaneous dosing with the antibody D2E7 and methotrexate every other week (bottom) for a total of twenty-four weeks. These data indicate that every other week dosing is as effective as every week dosing.
Figure 1:
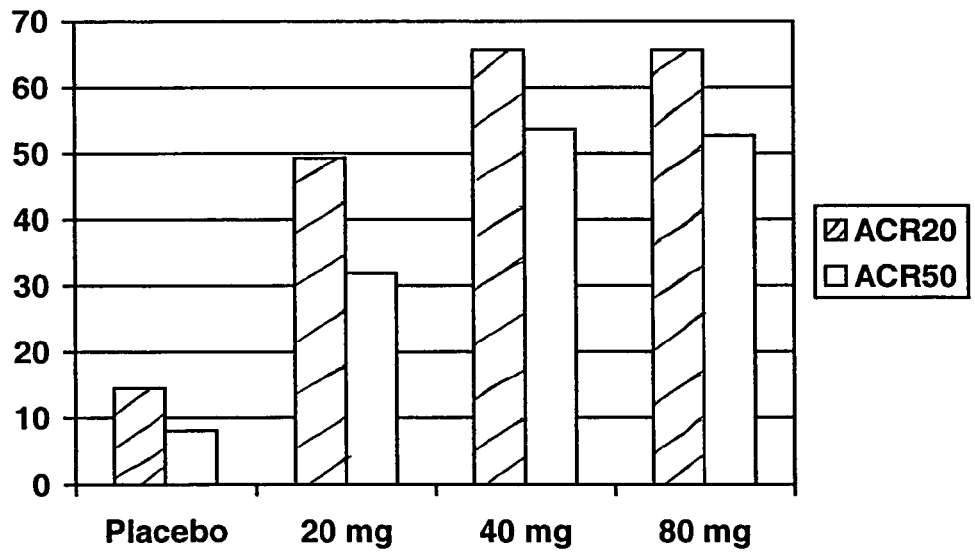

This invention pertains to methods of treating disorders in which the administration of an anti-TNFα antibody is beneficial comprising the administration of isolated human antibodies, or antigen-binding portions thereof, that bind to human TNFα with high affinity, a low off rate and high neutralizing capacity such that the disorder is treated. Various aspects of the invention relate to treatment with antibodies and antibody fragments, and pharmaceutical compositions thereof.

In order that the present invention may be more readily understood, certain terms are first defined.

The term "dosing", as used herein, refers to the administration of a substance (e.g., an anti-TNFα antibody) to achieve a therapeutic objective (e.g., the treatment of a TNFα-associated disorder).

The terms "biweekly dosing regimen", "biweekly dosing", and "biweekly administration", as used herein, refer to the time course of administering a substance (e.g., an anti-TNFα antibody) to a subject to achieve a therapeutic objective (e.g., the treatment of a TNFα-associated disorder). The biweekly dosing regimen is not intended to include a weekly dosing regimen. Preferably, the substance is administered every 9-19 days, more preferably, every 11-17 days, even more preferably, every 13-15 days, and most preferably, every 14 days.

The term "combination therapy", as used herein, refers to the administration of two or more therapeutic substances, e.g., an anti-TNFα antibody and the drug methotrexate. The methotrexate may be administered concomitant with, prior to, or following the administration of an anti-TNFα antibody.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of TNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.).

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo, for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II, below), antibodies isolated from a recombinant, combinatorial human antibody library (described further in Section III, below), antibodies isolated from an animal (e.g., a mouse) that is transgenic for human immunoglobulin genes (see e.g., Taylor, L. D., et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as hTNFα molecules from other species (discussed in further detail below). Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see Example 4). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 and Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind hTNFα, is intended to refer to a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, for example, an isolated nucleic acid of the invention encoding a VH region of an anti-hTNFα antibody contains no other sequences encoding other VH regions that bind antigens other than hTNFα.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Various aspects of the invention are described in further detail in the following subsections.

I. Human Antibodies that Bind Human TNFα

This invention provides methods of treating disorders in which the administration of an anti-TNFα antibody is beneficial. These methods include the biweekly, subcutaneous administration of isolated human antibodies, or antigen-binding portions thereof, that bind to human TNFα with high affinity, a low off rate and high neutralizing capacity. Preferably, the human antibodies of the invention are recombinant, neutralizing human anti-hTNFα antibodies. The most preferred recombinant, neutralizing antibody of the invention is referred to herein as D2E7 (the amino acid sequence of the D2E7 VL region is shown in SEQ ID NO: 1; the amino acid sequence of the D2E7 VH region is shown in SEQ ID NO: 2). The properties of D2E7 have been described in Salfeld et al., U.S. Pat. No. 6,090,382, which is incorporated by reference herein.

In one aspect, the invention pertains to treating disorders in which the administration of an anti-TNFα antibody is beneficial. These treatments include the biweekly, subcutaneous administration of D2E7 antibodies and antibody portions, D2E7-related antibodies and antibody portions, and other human antibodies and antibody portions with equivalent properties to D2E7, such as high affinity binding to hTNFα with low dissociation kinetics and high neutralizing capacity. In one embodiment, the invention provides treatment with an isolated human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. More preferably, the isolated human antibody, or antigen-binding portion thereof, dissociates from human TNFα with a $K_{off}$ of $5\times10^{-4}$ s$^{-1}$ or less, or even more preferably, with a $K_{off}$ of $1\times10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1\times10^{-8}$ M or less, even more preferably with an IC$_{50}$ of $1\times10^{-9}$ M or less and still more preferably with an IC$_{50}$ of $1\times10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to methods of treating disorders in which the administration of an anti-TNFα antibody is beneficial by subcutaneous administration of human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the invention provides methods of treating disorders in which the administration of an anti-TNFα antibody is beneficial by the biweekly, subcutaneous administration of an isolated human antibody, or antigen-binding portion thereof. The antibody or antigen-binding portion thereof preferably contains the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ s$^{-1}$ or less. Even more preferably, the antibody, or antigen-binding portion thereof, dissociates from human TNFα, with a $K_{off}$ of $1 \times 10^{-4}$ s$^{-1}$ or less.

In yet another embodiment, the invention provides methods of treating disorders in which the administration of an anti-TNFα antibody is beneficial by the biweekly, subcutaneous administration of an isolated human antibody, or an antigen-binding portion thereof. The antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_K$I human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_H$3 human germline family, more preferably from the DP-31 human germline VH gene and most preferably from the D2E7 VH framework sequences shown in FIGS. 2A and 2B U.S. Pat. No. 6,090,382.

In still another embodiment, the invention provides methods of treating disorders in which the administration of an anti-TNFα antibody is beneficial by the biweekly, subcutaneous administration of an isolated human antibody, or an antigen binding portion thereof. The antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention provides methods of treating disorders in which the administration of an anti-TNFα antibody is beneficial by the biweekly, subcutaneous administration of an isolated human antibody, or an antigen-binding portions thereof. The antibody or antigen-binding portion thereof preferably contains D2E7-related VL and VH CDR3 domains, for example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

An antibody or antibody portion of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

II. Expression of Antibodies

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express D2E7 or a D2E7-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest*, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_K I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

III. Selection of Recombinant Human Antibodies

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J.* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in Section II above.

IV. Pharmaceutical Compositions and Pharmaceutical Administration

The antibodies and antibody-portions of the invention can be incorporated into pharmaceutical compositions suitable for administration to a subject for the methods described herein, e.g., biweekly, subcutaneous dosing. Typically, the pharmaceutical composition comprises an antibody (or antibody portion) of the invention and/or methotrexate and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible and are suitable for administration to a subject for the methods described herein. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular injection. In a particularly preferred embodiment, the antibody is administered by subcutaneous injection (e.g., a biweekly, subcutaneous injection).

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyethylene glycol (PEG), polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents. For example, an anti-hTNFα antibody or antibody portion of the invention may be coformulated and/or coadministered with methotrexate, one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. The use of the antibodies, or antibody portions, of the invention in combination with other therapeutic agents is discussed further in subsection IV.

Non-limiting examples of therapeutic agents for rheumatoid arthritis with which an antibody, or antibody portion, of the invention can be combined include the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; J. Invest. Med. (1996) Vol. 44, 235A); 55 kdTNFR-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, 185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); TNF-bp/s-TNFR (soluble TNF binding protein; see e.g., *Arthritis & Rheumatism* (1996) Vol. 39, No. 9 (supplement), 5284; *Amer. J. Physiol.—Heart and Circulatory Physiology* (1995) Vol. 268, pp. 37-42); R973401 (phosphodiesterase Type IV inhibitor; see e.g., *Arthritis & Rheumatism* (1996) Vol. 39 No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), S282) and thalidomide-related drugs (e.g., Celgen); leflunomide (anti-inflammatory and cytokine inhibitor; see e.g., *Arthritis & Rheumatism* (1996) Vol. 39, No. 9 (supplement), S131; *Inflammation Research* (1996) Vol. 45, pp. 103-107); tranexamic acid (inhibitor of plasminogen activation; see e.g., *Arthritis & Rheumatism* (1996) Vol. 39, No. 9 (supplement), S284); T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; hydroxychloroquine; chlorambucil; cyclophosphamide; cyclosporine; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chloro-deoxyadenosine); and azaribine.

Non-limiting examples of therapeutic agents for inflammatory bowel disease with which an antibody, or antibody portion, of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; J. Invest. Med. (1996) Vol. 44, 235A); 55 kdTNFR-IgG (55 kD TNF receptor-IgG fusion protein; Hoffmann-LaRoche); interleukin-10 (SCH 52000; Schering Plough); IL-4; IL-10 and/or IL-4 agonists (e.g., agonist antibodies); interleukin-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

Nonlimiting examples of therapeutic agents for multiple sclerosis with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (Avonex™; Biogen); interferon-β1b (Betaseron™; Chiron/Berlex); Copolymer 1 (Cop-1; Copaxone™; Teva Pharmaceutical Industries, Inc.); hyperbaric oxygen; intravenous immunoglobulin; clabribine; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; J. Invest. Med. (1996) Vol. 44, 235A); 55 kdTNFR-IgG (55 kD TNF receptor-IgG fusion protein; Hoffmann-LaRoche); IL-10; IL-4; and IL-10 and/or IL-4 agonists (e.g., agonist antibodies).

Nonlimiting examples of therapeutic agents for sepsis with which an antibody, or antibody portion, of the invention can be combined include the following: hypertonic saline solutions; antibiotics; intravenous gamma globulin; continuous hemofiltration; carbapenems (e.g., meropenem); antagonists of cytokines such as TNFα, IL-1β, IL-6 and/or IL-8; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; J. Invest. Med. (1996) Vol. 44, 235A); 55 kdTNFR-IgG (55 kD TNF receptor-IgG fusion protein; Hoffmann-LaRoche); Cytokine Regulating Agents (CRAs) HP228 and HP466 (Houghten Pharmaceuticals, Inc.); SK&F 107647 (low molecular peptide; SmithKline Beecham); tetravalent guanylhydrazone CNI-1493 (Picower Institute); Tissue Factor Pathway Inhibitor (TFPI; Chiron); PHP (chemically modified hemoglobin; APEX Bioscience); iron chelators and chelates, including diethylenetriamine pentaacetic acid-iron (III) complex (DTPA iron (III); Molichem Medicines); lisofylline (synthetic small molecule methylxanthine; Cell Therapeutics, Inc.); PGG-Glucan (aqeuous soluble β1,3glucan; Alpha-Beta Technology); apolipoprotein A-1 reconstituted with lipids; chiral hydroxamic acids (synthetic antibacterials that inhibit lipid A biosynthesis); anti-endotoxin antibodies; E5531 (synthetic lipid A antagonist; Eisai America, Inc.); rBPI$_{21}$ (recombinant N-terminal fragment of human Bactericidal/Permeability-Increasing Protein); and Synthetic Anti-Endotoxin Peptides (SAEP; BiosYnth Research Laboratories);

Nonlimiting examples of therapeutic agents for adult respiratory distress syndrome (ARDS) with which an antibody, or antibody portion, of the invention can be combined include the following: anti-IL-8 antibodies; surfactant replacement therapy; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37, S295; J. Invest. Med. (1996) Vol. 44, 235A); and 55 kdTNFR-IgG (55 kD TNF receptor-IgG fusion protein; Hoffmann-LaRoche).

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 10-100 mg, more preferably 20-80 mg and most preferably about 40 mg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

V. Uses of the Antibodies of the Invention

Given their ability to bind to hTNFα, the anti-hTNFα antibodies, or portions thereof, of the invention can be used to detect hTNFα (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting hTNFα in a biological sample comprising contacting a biological sample with an antibody, or antibody portion, of the invention and detecting either the antibody (or antibody portion) bound to hTNFα or unbound antibody (or antibody portion), to thereby detect hTNFα in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

Alternative to labeling the antibody, hTNFα can be assayed in biological fluids by a competition immunoassay utilizing rhTNFα standards labeled with a detectable substance and an unlabeled anti-hTNFα antibody. In this assay, the biological sample, the labeled rhTNFα standards and the anti-hTNFα antibody are combined and the amount of labeled rhTNFα standard bound to the unlabeled antibody is determined. The amount of hTNFα in the biological sample is inversely proportional to the amount of labeled hTNFα standard bound to the anti-hTNFα antibody.

A D2E7 antibody of the invention can also be used to detect TNFαs from species other than humans, in particular TNFαs from primates (e.g., chimpanzee, baboon, marmoset, cynomolgus and rhesus), pig and mouse, since D2E7 can bind to each of these TNFαs.

The antibodies and antibody portions of the invention are capable of neutralizing hTNFα activity both in vitro and in vivo (see U.S. Pat. No. 6,090,382). Moreover, at least some of the antibodies of the invention, such as D2E7, can neutralize hTNFα activity from other species. Accordingly, the antibodies and antibody portions of the invention can be used to inhibit hTNFα activity, e.g., in a cell culture containing hTNFα, in human subjects or in other mammalian subjects having TNFαs with which an antibody of the invention cross-reacts (e.g. chimpanzee, baboon, marmoset, cynomolgus and rhesus, pig or mouse). In one embodiment, the invention provides a method for inhibiting TNFα activity comprising contacting TNFα with an antibody or antibody portion of the invention such that TNFα activity is inhibited. Preferably, the TNFα is human TNFα. For example, in a cell culture containing, or suspected of containing TNFα, an antibody or antibody portion of the invention can be added to the culture medium to inhibit hTNFα activity in the culture.

In a preferred embodiment, the invention provides methods of treating disorders in which the administration of an anti-TNFα antibody is beneficial, comprising subcutaneously administering to the subject biweekly an antibody or antibody portion of the invention such that the disorder is treated. In a particularly preferred embodiment, the antibody is administered subcutaneously on a biweekly schedule. In another particularly preferred embodiment, the antibody is administered subcutaneously before, during or after administration of methotrexate. Preferably, the subject is a human subject. Alternatively, the subject can be a mammal expressing a TNFα with which an antibody of the invention cross-reacts. Still further the subject can be a mammal into which has been introduced hTNFα (e.g., by administration of hTNFα or by expression of an hTNFα transgene). An antibody of the invention can be administered to a human subject for therapeutic purposes (discussed further below). Moreover, an antibody of the invention can be administered to a non-human mammal expressing a TNFα with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which the administration of an anti-TNFα antibody is beneficial" is intended to include diseases and other disorders in which the presence of TNFα in a subject suffering from the disorder has been shown to be or is suspected of being either responsible for the pathophysiology of the disorder or a factor that contributes to a worsening of the disorder, or where it has been shown that another anti-TNFα antibody or a biologically active portion thereof has been successfully used to treat the disease. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above. There are numerous examples of disorders in which TNFα activity is detrimental. The use of the antibodies and antibody portions of the invention in the treatment of specific disorders is discussed further below:

A. Sepsis

Tumor necrosis factor has an established role in the pathophysiology of sepsis, with biological effects that include hypotension, myocardial suppression, vascular leakage syndrome, organ necrosis, stimulation of the release of toxic secondary mediators and activation of the clotting cascade (see e.g., Tracey, K. J. and Cerami, A. (1994) *Annu. Rev. Med.* 45:491-503; Russell, D. and Thompson, R. C. (1993) *Curr. Opin. Biotech.* 4:714-721).

Accordingly, the human antibodies, and antibody portions, of the invention can be used to treat sepsis in any of its clinical settings, including septic shock, endotoxic shock, gram negative sepsis and toxic shock syndrome.

Furthermore, to treat sepsis, an anti-hTNFα antibody, or antibody portion, of the invention can be coadministered with one or more additional therapeutic agents that may further alleviate sepsis, such as an interleukin-1 inhibitor (such as those described in PCT Publication Nos. WO 92/16221 and WO 92/17583), the cytokine interleukin-6 (see e.g., PCT Publication No. WO 93/11793) or an antagonist of platelet activating factor (see e.g., European Patent Application Publication No. EP 374 510).

Additionally, in a preferred embodiment, an anti-TNFα antibody or antibody portion of the invention is administered to a human subject within a subgroup of sepsis patients having a serum or plasma concentration of IL-6 above 500 pg/ml, and more preferably 1000 pg/ml, at the time of treatment (see PCT Publication No. WO 95/20978 by Daum, L., et al.).

B. Autoimmune Diseases

Tumor necrosis factor has been implicated in playing a role in the pathophysiology of a variety of autoimmune diseases. For example, TNFα has been implicated in activating tissue inflammation and causing joint destruction in rheumatoid arthritis (see e.g., Tracey and Cerami, supra; Arend, W. P. and Dayer, J-M. (1995) *Arth. Rheum.* 38:151-160; Fava, R. A., et al. (1993) *Clin. Exp. Immunol.* 94:261-266). TNFα also has been implicated in promoting the death of islet cells and in mediating insulin resistance in diabetes (see e.g., Tracey and Cerami, supra; PCT Publication No. WO 94/08609). TNFα also has been implicated in mediating cytotoxicity to oligodendrocytes and induction of inflammatory plaques in multiple sclerosis (see e.g., Tracey and Cerami, supra). Chimeric and humanized murine anti-hTNFα antibodies have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

The human antibodies, and antibody portions of the invention can be used to treat autoimmune diseases, in particular those associated with inflammation, including rheumatoid arthritis, rheumatoid spondylitis, osteoarthritis and gouty arthritis, allergy, multiple sclerosis, autoimmune diabetes, autoimmune uveitis and nephrotic syndrome. Typically, the antibody, or antibody portion, is administered systemically, although for certain disorders, local administration of the antibody or antibody portion at a site of inflammation may be beneficial (e.g., local administration in the joints in rheumatoid arthritis or topical application to diabetic ulcers, alone or in combination with a cyclohexane-ylidene derivative as described in PCT Publication No. WO 93/19751).

C. Infectious Diseases

Tumor necrosis factor has been implicated in mediating biological effects observed in a variety of infectious diseases. For example, TNFα has been implicated in mediating brain inflammation and capillary thrombosis and infarction in malaria (see e.g., Tracey and Cerami, supra). TNFα also has been implicated in mediating brain inflammation, inducing breakdown of the blood-brain barrier, triggering septic shock syndrome and activating venous infarction in meningitis (see e.g., Tracey and Cerami, supra). TNFα also has been implicated in inducing cachexia, stimulating viral proliferation and mediating central nervous system injury in acquired immune deficiency syndrome (AIDS) (see e.g., Tracey and Cerami, supra). Accordingly, the antibodies, and antibody portions, of the invention, can be used in the treatment of infectious diseases, including bacterial meningitis (see e.g., European Patent Application Publication No. EP 585 705), cerebral malaria, AIDS and AIDS-related complex (ARC) (see e.g., European Patent Application Publication No. EP 230 574), as well as cytomegalovirus infection secondary to transplantation (see e.g., Fietze, E., et al. (1994) *Transplantation* 58:675-680). The antibodies, and antibody portions, of the invention, also can be used to alleviate symptoms associated with infectious diseases, including fever and myalgias due to infection (such as influenza) and cachexia secondary to infection (e.g., secondary to AIDS or ARC).

D. Transplantation

Tumor necrosis factor has been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants (see e.g., Tracey and Cerami, supra; Eason, J. D., et al. (1995) *Transplantation* 59:300-305; Suthanthiran, M. and Strom, T. B. (1994) *New Engl. J. Med.* 331:365-375). Accordingly, the antibodies, and antibody portions, of the invention, can be used to inhibit transplant rejection, including rejections of allografts and xenografts and to inhibit GVHD. Although the antibody or antibody portion may be used alone, more preferably it is used in combination with one or more other agents that inhibit the immune response against the allograft or inhibit GVHD. For example, in one embodiment, an antibody or antibody portion of the invention is used in combination with OKT3 to inhibit OKT3-induced reactions. In another embodiment, an antibody or antibody portion of the invention is used in combination with one or more antibodies directed at other targets involved in regulating immune responses, such as the cell surface molecules CD25 (interleukin-2 receptor-α), CD11a (LFA-1), CD54 (ICAM-1), CD4, CD45, CD28/CTLA4, CD80 (B7-1) and/or CD86 (B7-2). In yet another embodiment, an antibody or antibody portion of the invention is used in combination with one or more general immunosuppressive agents, such as cyclosporin A or FK506.

E. Malignancy

Tumor necrosis factor has been implicated in inducing cachexia, stimulating tumor growth, enhancing metastatic potential and mediating cytotoxicity in malignancies (see e.g., Tracey and Cerami, supra). Accordingly, the antibodies, and antibody portions, of the invention, can be used in the treatment of malignancies, to inhibit tumor growth or metastasis and/or to alleviate cachexia secondary to malignancy. The antibody, or antibody portion, may be administered systemically or locally to the tumor site.

F. Pulmonary Disorders

Tumor necrosis factor has been implicated in the pathophysiology of adult respiratory distress syndrome, including stimulating leukocyte-endothelial activation, directing cytotoxicity to pneumocytes and inducing vascular leakage syndrome (see e.g., Tracey and Cerami, supra). Accordingly, the antibodies, and antibody portions, of the invention, can be used to treat various pulmonary disorders, including adult respiratory distress syndrome (see e.g., PCT Publication No. WO 91/04054), shock lung, chronic pulmonary inflammatory disease, pulmonary sarcoidosis, pulmonary fibrosis and silicosis. The antibody, or antibody portion, may be administered systemically or locally to the lung surface, for example as an aerosol.

G. Intestinal Disorders

Tumor necrosis factor has been implicated in the pathophysiology of inflammatory bowel disorders (see e.g., Tracy, K. J., et al. (1986) *Science* 234:470-474; Sun, X-M., et al. (1988) *J. Clin. Invest.* 81:1328-1331; MacDonald, T. T., et al. (1990) *Clin. Exp. Immunol.* 81:301-305). Chimeric murine anti-hTNFα antibodies have undergone clinical testing for treatment of Crohn's disease (van Dullemen, H. M., et al. (1995) *Gastroenterology* 109:129-135). The human antibodies, and antibody portions, of the invention, also can be used to treat intestinal disorders, such as idiopathic inflammatory bowel disease, which includes two syndromes, Crohn's disease and ulcerative colitis.

H. Cardiac Disorders

The antibodies, and antibody portions, of the invention, also can be used to treat various cardiac disorders, including ischemia of the heart (see e.g., European Patent Application Publication No. EP 453 898) and heart insufficiency (weakness of the heart muscle) (see e.g., PCT Publication No. WO 94/20139).

I. Others

The antibodies, and antibody portions, of the invention, also can be used to treat various other disorders in which TNFα activity is detrimental. Examples of other diseases and disorders in which TNFα activity has been implicated in the pathophysiology, and thus which can be treated using an antibody, or antibody portion, of the invention, include inflammatory bone disorders and bone resorption disease (see e.g., Bertolini, D. R., et al. (1986) *Nature* 319:516-518; Konig, A., et al. (1988) *J. Bone Miner. Res.* 3:621-627; Lerner, U. H. and Ohlin, A. (1993) *J. Bone Miner. Res.* 8:147-155; and Shankar, G. and Stern, P. H. (1993) *Bone* 14:871-876), hepatitis, including alcoholic hepatitis (see e.g., McClain, C. J. and Cohen, D. A. (1989) *Hepatology* 9:349-351; Felver, M. E., et al. (1990) *Alcohol. Clin. Exp. Res.* 14:255-259; and Hansen, J., et al. (1994) *Hepatology* 20:461-474) and viral hepatitis (Sheron, N., et al. (1991) *J. Hepatol.* 12:241-245; and Hussain, M. J., et al. (1994) *J. Clin. Pathol.* 47:1112-1115), coagulation disturbances (see e.g., van der Poll, T., et al. (1990) *N. Engl. J. Med.* 322:1622-1627; and van der Poll, T., et al. (1991) *Prog. Clin. Biol. Res.* 367:55-60), burns (see e.g., Giroir, B. P., et al. (1994) *Am. J. Physiol.* 267:H118-124; and Liu, X. S., et al. (1994) *Burns* 20:40-44), reperfusion injury (see e.g., Scales, W. E., et al. (1994) Am. J. Physiol. 267:G1122-1127; Serrick, C., et al. (1994) *Transplantation* 58:1158-1162; and Yao, Y. M., et al. (1995) *Resuscitation* 29:157-168), keloid formation (see e.g., McCauley, R. L., et al. (1992) *J. Clin. Immunol.* 12:300-308), scar tissue formation and pyrexia.

This invention is further illustrated by the following examples which should not be construed as limiting. The contents of all references, patents and published patent applications cited throughout this application are hereby incorporated by reference.

Example 1

Treatment with an Anti-TNFα Antibody

D2E7 Efficacy Following Subcutaneous Administration

In this study, twenty-four patients with active RA were treated with weekly doses of 0.5 mg/kg D2E7 (n=18) or placebo (n=6) by s.c. injection for three months. Patients participating in this study had a mean duration of disease of 10.1 years with a disease activity score (DAS) score of 4.87 and a mean of 3.4 DMARDs (disease modifying anti-rheumatic drugs) prior to study entry; again reflecting considerable disease activity. Responders continued open-label treatment with D2E7, while patients who failed to respond to the 0.5 mg/kg dose or who lost a DAS response on the 0.5 mg/kg dose were escalated to receive 1 mg/kg by s.c. injection after week twelve of the study.

The first patients enrolled received up to sixty injections and were, therefore, sixty weeks on the study drug. The efficacy with s.c. dosing was similar to i.v. injections. Up to 78% of patients reached a DAS and ACR20 response during the first weeks of treatment. Subcutaneous D2E7 at a dose of 0.5 mg/kg/week reduced the swollen joint (SWJ) count by 54%, tender joint count (TJC) by 61% and CRP by 39% over twelve weeks compared to baseline, whereas all parameters increased in the placebo group. After completion of the placebo-controlled period of this study, the patients continued treatment for up to fourteen months with sustained efficacy. These results indicate that subcutaneous D2E7 at a dose of 0.5 mg/kg/week can, therefore, be safely self-administered with good local tolerability.

Administration of D2E7 and Methotrexate

In this study, patients received s.c. or i.v. placebo or D2E7 at a dose of 1 mg/kg in addition to their ongoing treatment with (methotrexate) MTX. Fifty-four patients were enrolled in the study and eighteen patients received i.v. D2E7 and s.c. placebo, eighteen patients received i.v. placebo and s.c. D2E7, and eighteen patients received placebo i.v. and s.c. The patients received their second dose only after they lost their blinded response status, not earlier than four weeks after the first dose. Thereafter, all patients received open-label biweekly s.c. injections of D2E7.

Figure 5:
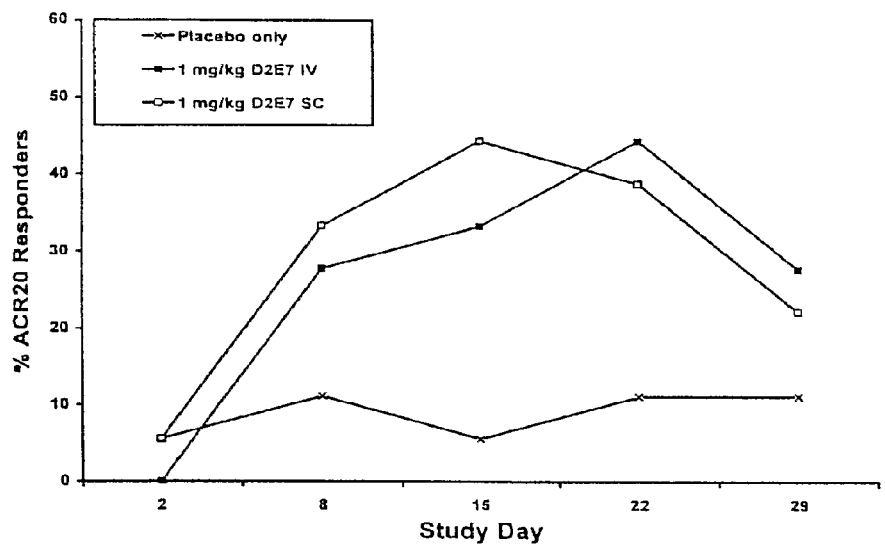
FIG. 5 depicts the percentage of ACR responders following a single intravenous injection of the antibody D2E7 and methotrexate in patients suffering from RA.

Demographic characteristics of the study population of this study included a mean duration of RA of 11.1 years, prior exposure to a mean of 3.6 DMARDs (other than MTX), and a mean DAS at study entry of 4.81. By Day twenty-nine, 72% of the i.v. D2E7 treated patients and 44% of the s.c. D2E7 treated patients had achieved a response by DAS criteria, compared to only 28% of placebo-treated patients (set forth in FIG. 5). Of the responders in this study, 28% of placebo treated patients maintained an ACR20 response up to day 29, compared to 72% of i.v.-treated D2E7 patients and 67% of s.c.-treated D2E7 patients, who maintained their responses for between one and three months.

Example 2

Total Body Dose of a Subcutaneously Administered Anti-TNFα Antibody

Weekly, Subcutaneous Administration of D2E7

This study enrolled two hundred eighty-four patients with RA and was designed to determine the optimal total body dose of subcutaneously administered D2E7. Patients were randomized to receive either 20, 40, or 80 mg D2E7 or placebo weekly for twelve weeks, after which time placebo-treated patients were switched blindly to 40 mg D2E7/week.

Figure 2:
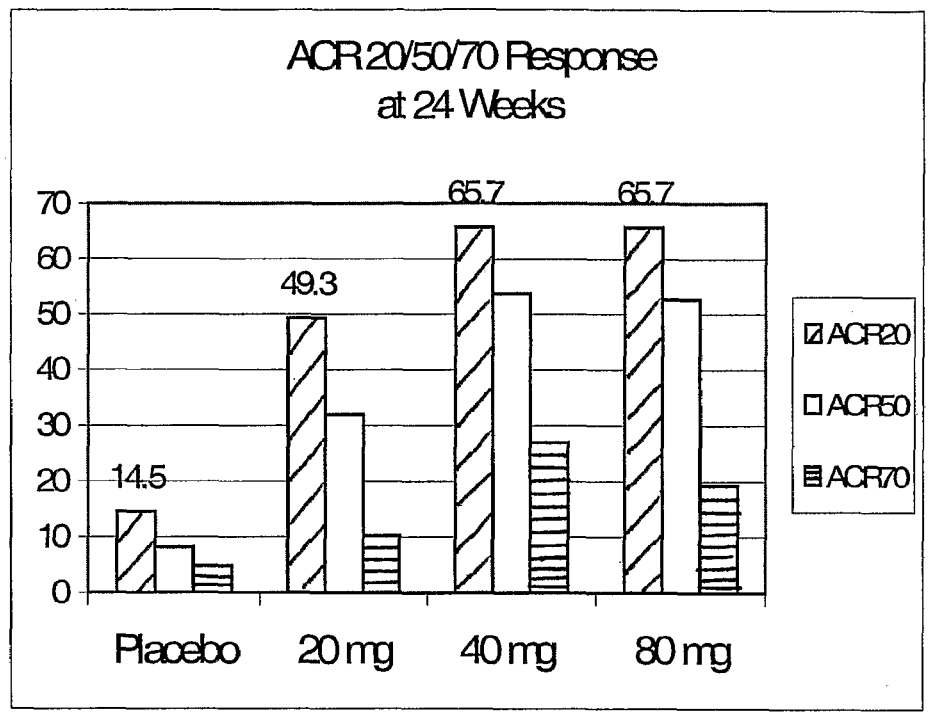
FIG. 2 depicts ACR20, ACR50, and ACR70 responses for patients suffering from RA after subcutaneous dosing with the antibody D2E7 and methotrexate every other week at twenty-four weeks.
Figure 3A:
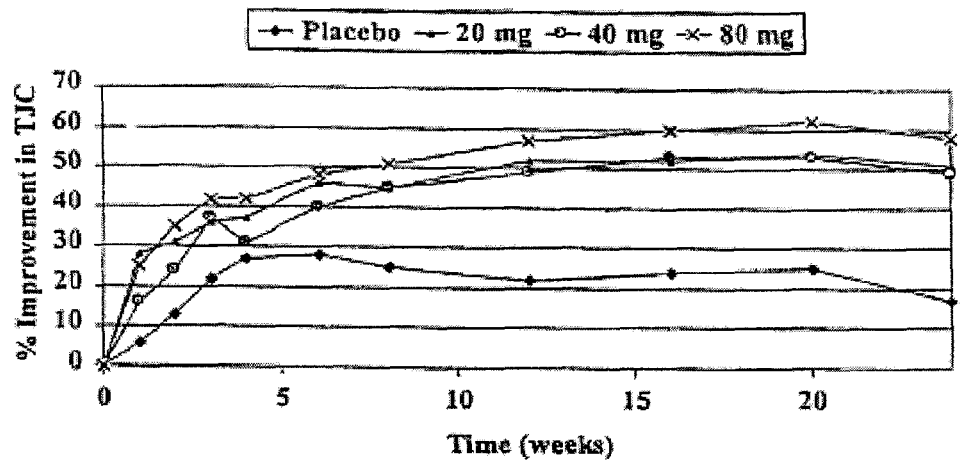
FIGS. 3A and 3B depict time courses of tender joint count (3A) and swollen joint count (3B) over twenty-four weeks for patients suffering from RA after subcutaneous dosing with D2E7 and methotrexate every other week at twenty-four weeks.
Figure 3B:
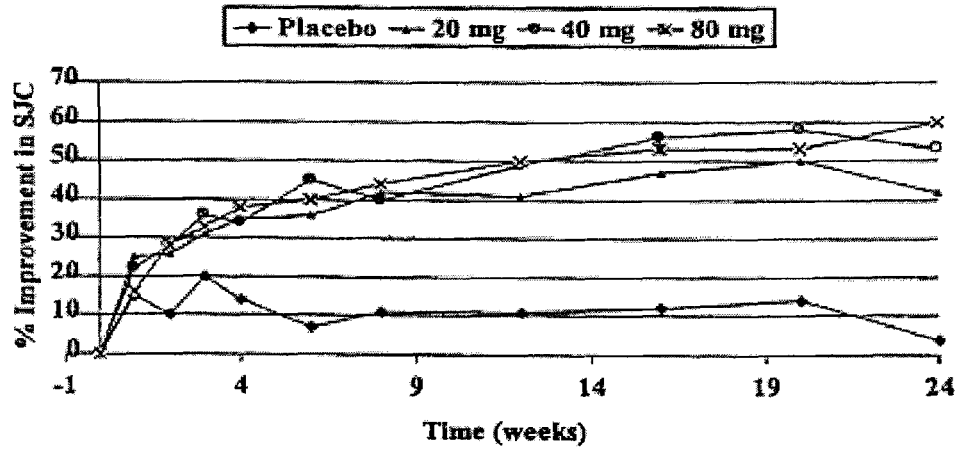
Figure 4A:
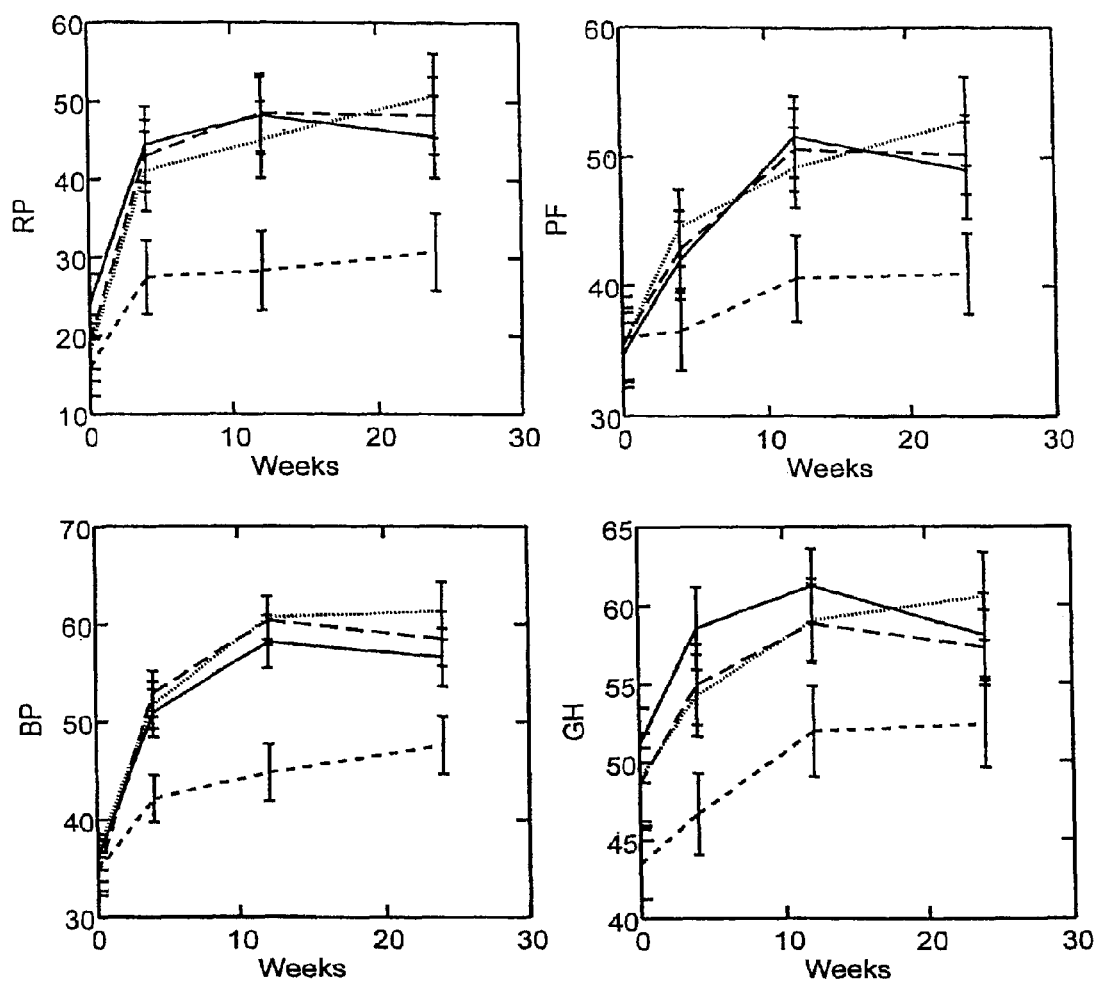
FIGS. 4A and 4B depict results from a short form health survey (SF-36) from patients suffering from RA after subcutaneous dosing with the antibody D2E7 and methotrexate every other week at twenty-four weeks. RP, role physical; PF, physical function; BP, bodily pain; GH, general health; V, vitality; SF, social functioning; RE, role emotional; and ME, mental health.
Figure 4B:
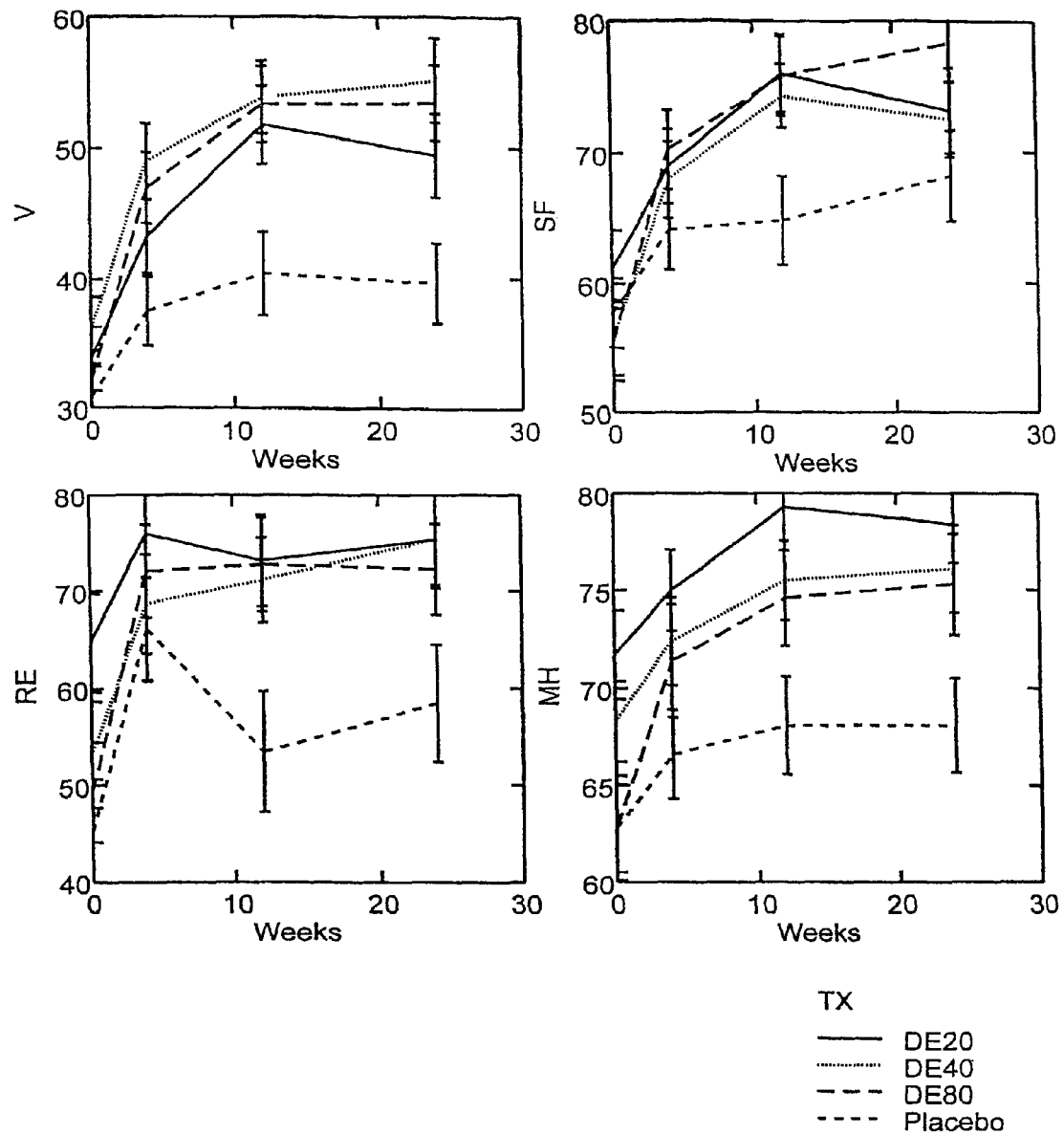

Approximately 49% of patients reached ACR20 at 20 mg, 55% of patients reached ACR20 at 40 mg, and 54% of patients reached ACR20 at 80 mg, while only 10% of patients receiving placebo reached ACR20 (set forth in FIG. 1A). Approximately 23% of patients reached ACR50 at 20 mg, 27% of patients reached ACR50 at 40 mg, and 20% of patients reached ACR50 at 80 mg, and only 2% of patients receiving placebo reached ACR50. These data illustrate that subcutaneous D2E7, particularly at a dose of 40 mg/week, generates a good response.

Example 3

Biweekly, Subcutaneous Administration of an Anti-TNFα Antibody

Biweekly, Subcutaneous Administration of D2E7

The clinical effects, safety, immunogenicity, and tolerance of RA patients with partial responses to MTX following every other week subcutaneous (s.c.) injections of placebo or D2E7 at several dose levels for up to twenty-four weeks in conjunction with continued MTX treatment was investigated.

Study Design

A placebo-controlled, double-blind, randomized, multi-center study in patients with RA, who had insufficient efficacy or tolerability to MTX was performed. During the course of the trial, patients were continued on a stable dose of MTX with dose ranges specified in the inclusion criteria described below.

This study consisted of two portions: 1) a "wash-out period" of four weeks prior to the administration of the first dose medication, during which time DMARDs (except for MTX) were withdrawn; and 2) a "placebo controlled period" during which time patients were randomized to one of four cohorts of sixty-seven patients to receive placebo, 20, 40, or 80 mg D2E7 (as a total body dose) given every other week s.c. for up to 24 weeks. Each dose of study drug was administered as two s.c. injections of 1.6 mL each. The patient's first dose was administered by medical personnel as part of the patient's training. Subsequent doses were self-administered by the patient at the study under the direct observation of trained personnel for the first four weeks. Thereafter, doses were administered outside the study site by the patient, a trained individual designated by the patient, or by medical personnel. Medication for four or five weeks was dispensed after each clinical assessment. Patients were serially examined in weeks one, two, three, four, six, eight, twelve, sixteen, twenty, and twenty-four of the study with the joint examinations being performed by a blinded assessor, independent of the treating physician.

This study enrolled two hundred seventy-one patients with RA. The study population was representative of the moderate to severe RA population in North America: approximately 70% female, and predominantly over the age of forty. The population was selected using predetermined inclusion and exclusion criteria, known to those of skill in the art e.g., a patient must have received a diagnosis of RA as defined by the 1987-revised American College of Rheumatology (ACR) criteria (set forth in Appendix A)

Results

FIGS. 1B and 2-4 indicate that subcutaneous, biweekly D2E7 treatment combined with methotrexate was significantly better than placebo in reducing the signs and symptoms of RA at twenty-four weeks. All three doses of D2E7 were statistically significantly more effective than placebo given weekly. Furthermore, D2E7 at 40 mg and 80 mg had better efficacy than the 20 mg dose.

EQUIVALENTS

Those skilled in the art will recognize, or be able to ascertain using no more than routine experimentation, many equivalents to the specific embodiments of the invention described herein. Such equivalents are intended to be encompassed by the following claims.

ACR Definition of RA

The 1987 classification tree criteria and functions for rheumatoid arthritis (RA)

| CRITERION | DEFINITION |
|---|---|
| 1. Arthritis of 3 or more joint areas | At least 3 joint areas simultaneously have had soft tissues swelling or fluid (not bony overgrowth alone) observed by a physician. The 14 possible joint areas are right or left PIP, MDP, wrist, elbow, knee, ankle, and MTP joints. |
| 2. Arthritis of hand joints<br>Wrist<br>MCP<br>MCP or wrist<br>MCP and wrist | Soft tissue swelling or fluid (not bony overgrowth alone) of the specified area observed by a physician. Where 2 areas are specified, involvement must have been simultaneous. |
| 3 Symmetric swelling (arthritis) | Simultaneous involvement of the same joint areas (as defined in 1 on both sides of the body (bilateral involvement of PIPs. MCP's, or MTPs is acceptable without absolute symmetry) |
| 4. Serum rheumatoid factor | Demonstration of abnormal amounts of serum rheumatoid factor by any method for which the result has been positive in <5% of normal control subjects |
| 5. Radiographic changes of rheumatoid arthritis | Radiographic changes typical of rheumatoid arthritis on posteroanterior hand and wrist radiographs which must include erosions or unequivocal bony decalcification localized in or most marked adjacent to the involved joints (Osteoarthritis changes alone do not qualify) |

A patient is said to have RA if he/she is included in 1 of the 5RA subsets listed in Table 7 and has a clinical diagnosis of RA by his/her physician. Criteria 1, 2, and 3 must have been present for at least 6 weeks.
Arthritis and Rheumatism, Vol. 31, No. 3 (March 1988)

APPENDIX A

```
SEQ ID NO: 1:
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Tyr
                20                  25                  30
Leu Ala Trp Tyr Gln Gln Lys Pro Gly Lys Ala Pro Lys Leu Leu Ile
            35                  40                  45
Tyr Ala Ala Ser Thr Leu Gln Ser Gly Val Pro Ser Arg Phe Ser Gly
50                      55                  60
Ser Gly Ser Gly Thr Asp Phe Thr Leu Thr Ile Ser Ser Leu Gln Pro
65                  70                  75                      80
Glu Asp Val Ala Thr Tyr Tyr Cys Gln Arg Tyr Asn Arg Ala Pro Tyr
                85                  90                  95
Thr Phe Gly Gln Gly Thr Lys Val Glu Ile Lys
            100                 105

SEQ ID NO: 2:
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
                20                  25                  30
Ala Met His Trp Val Arg Gln Ala Pro Gly Lys Gly Leu Glu Trp Val
            35                  40                  45
Ser Ala Ile Thr Trp Asn Ser Gly His Ile Asp Tyr Ala Asp Ser Val
50                      55                  60
Glu Gly Arg Phe Thr Ile Ser Arg Asp Asn Ala Lys Asn Ser Leu Tyr
65                  70                  75                      80
Leu Gln Met Asn Ser Leu Arg Ala Glu Asp Thr Ala Val Tyr Tyr Cys
                85                  90                  95
Ala Lys Val Ser Tyr Leu Ser Thr Ala Ser Ser Leu Asp Tyr Trp Gly
            100                 105                 110
Gln Gly Thr Leu Val Thr Val Ser Ser
            115                 120

SEQ ID NO: 3:
Gln Arg Tyr Asn Arg Ala Pro Tyr Xaa
1               5
```

APPENDIX B

```
SEQ ID NO: 4:
Val Ser Tyr Leu Ser Thr Ala Ser Ser Leu Asp Xaa
 1              5                   10
Xaa of SEQ ID NO: 4 = Tyr or Asn

SEQ ID NO: 5:
Ala Ala Ser Thr Leu Gln Ser
1               5

SEQ ID NO: 6:
Ala Ile Thr Trp Asn Ser Gly His Ile Asp Tyr Ala Asp Ser Val Glu
1               5                   10                  15
Gly

SEQ ID NO: 7:
Arg Ala Ser Gln Gly Ile Arg Asn Tyr Leu Ala
1               5                   10

SEQ ID NO: 8:
Asp Tyr Ala Met His
1               5

SEQ ID NO: 9:
Asp Ile Gln Met Thr Gln Ser Pro Ser Ser Leu Ser Ala Ser Ile Gly
1               5                   10                  15
Asp Arg Val Thr Ile Thr Cys Arg Ala Ser Gln Gly Ile Arg Asn Tyr
                20                  25                  30
Leu Ala Trp Tyr Gln Gln Lys Pro Gly Lys Ala Pro Lys Leu Leu Ile
            35                  40                  45
Tyr Ala Ala Ser Thr Leu Gln Ser Gly Val Pro Ser Arg Ile Ser Gly
50                      55                  60
Ser Gly Ser Gly Thr Asp Ile Thr Leu Thr Ile Ser Ser Leu Gln Pro
65                  70                  75                      80
Glu Asp Val Ala Thr Tyr Tyr Cys Gln Lys Tyr Asn Ser Ala Pro Tyr
                85                  90                  95
Ala Ile Gly Gln Gly Thr Lys Val Glu Ile Lys
            100                 105
```

APPENDIX B-continued

SEQ ID NO: 10:
```
Gln Val Gln Leu Val Glu Ser Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Asp Trp Val
            35                  40                  45
Ser Ala Ile Thr Trp Asn Ser Gly His Ile Asp Tyr Ala Asp Ser Val
        50                  55                  60
Glu Gly Arg Phe Ala Val Ser Arg Asp Asn Ala Lys Asn Ala Leu Tyr
65                  70                  75                  80
Leu Gln Met Asn Ser Leu Arg Pro Glu Asp Thr Ala Val Tyr Tyr Cys
                85                  90                  95
Thr Lys Ala Ser Tyr Leu Ser Thr Ser Ser Leu Asp Asn Trp Gly
            100                 105                 110
Gln Gly Thr Leu Val Thr Val Ser Ser
            115                 120
```

SEQ ID NO: 11:
```
Gln Lys Tyr Asn Ser Ala Pro Tyr Ala
1               5
```

SEQ ID NO: 12:
```
Gln Lys Tyr Asn Arg Ala Pro Tyr Ala
1               5
```

SEQ ID NO: 13:
```
Gln Lys Tyr Gln Arg Ala Pro Tyr Thr
1               5
```

SEQ ID NO: 14:
```
Gln Lys Tyr Ser Ser Ala Pro Tyr Thr
1               5
```

SEQ ID NO: 15:
```
Gln Lys Tyr Asn Ser Ala Pro Tyr Thr
1               5
```

SEQ ID NO: 16:
```
Gln Lys Tyr Asn Arg Ala Pro Tyr Thr
1               5
```

SEQ ID NO: 17:
```
Gln Lys Tyr Asn Ser Ala Pro Tyr Tyr
1               5
```

SEQ ID NO: 18:
```
Gln Lys Tyr Asn Ser Ala Pro Tyr Asn
1               5
```

SEQ ID NO: 19:
```
Gln Lys Tyr Thr Ser Ala Pro Tyr Thr
1               5
```

SEQ ID NO: 20:
```
Gln Lys Tyr Asn Arg Ala Pro Tyr Asn
1               5
```

SEQ ID NO: 21:
```
Gln Lys Tyr Asn Ser Ala Ala Tyr Ser
1               5
```

SEQ ID NO: 22:
```
Gln Gln Tyr Asn Ser Ala Pro Asp Thr
1               5
```

SEQ ID NO: 23:
```
Gln Lys Tyr Asn Ser Asp Pro Tyr Thr
1               5
```

SEQ ID NO: 24:
```
Gln Lys Tyr Ile Ser Ala Pro Tyr Thr
1               5
```

SEQ ID NO: 25:
```
Gln Lys Tyr Asn Arg Pro Pro Tyr Thr
1               5
```

SEQ ID NO: 26:

APPENDIX B-continued

```
Gln Arg Tyr Asn Arg Ala Pro Tyr Ala
 1               5

SEQ ID NO: 27:
Ala Ser Tyr Leu Ser Thr Ser Ser Ser Leu Asp Asn
 1               5                  10

SEQ ID NO: 28:
Ala Ser Tyr Leu Ser Thr Ser Ser Ser Leu Asp Lys
 1               5                  10

SEQ ID NO: 29:
Ala Ser Tyr Leu Ser Thr Ser Ser Ser Leu Asp Tyr
 1               5                  10

SEQ ID NO: 30:
Ala Ser Tyr Leu Ser Thr Ser Ser Ser Leu Asp Asp
 1               5                  10

SEQ ID NO: 31:
Ala Ser Tyr Leu Ser Thr Ser Phe Ser Leu Asp Tyr
 1               5                  10

SEQ ID NO: 32:
Ala Ser Tyr Leu Ser Thr Ser Ser Ser Leu His Tyr
 1               5                  10

SEQ ID NO: 33:
Ala Ser Phe Leu Ser Thr Ser Ser Ser Leu Glu Tyr
 1               5                  10

SEQ ID NO: 34:
Ala Ser Tyr Leu Ser Thr Ala Ser Ser Leu Glu Tyr
 1               5                  10

SEQ ID NO: 35:
Val Ser Tyr Leu Ser Thr Ala Ser Ser Leu Asp Asn
 1               5                  10

SEQ ID NO: 36:
GACATCCAGA TGACCCAGTC TCCATCCTCC CTGTCTGCAT CTGTAGGGGA CAGAGTCACC    60
ATCACTTGTC GGGCAAGTCA GGGCATCAGA AATTACTTAG CCTGGTATCA GCAAAAACCA   120
GGGAAAGCCC CTAAGCTCCT GATCTATGCT GCATCCACTT TGCAATCAGG GGTCCCATCT   180
CGGTTCAGTG GCAGTGGATC TGGGACAGAT TTCACTCTCA CCATCAGCAG CCTACAGCCT   240
GAAGATGTTG CAACTTATTA CTGTCAAAGG TATAACCGTG CACCGTATAC TTTTGGCCAG   300
GGGACCAAGG TGGAAATCAA A                                             321

SEQ ID NO: 37:
GAGGTGCAGC TGGTGGAGTC TGGGGGAGGC TTGGTACAGC CCGGCAGGTC CCTGAGACTC    60
TCCTGTGCGG CCTCTGGATT CACCTTTGAT GATTATGCCA TGCACTGGGT CCGGCAAGCT   120
CCAGGGAAGG GCCTGGAATG GGTCTCAGCT ATCACTTGGA ATAGTGGTCA CATAGACTAT   180
GCGGACTCTG TGGAGGGCCG ATTCACCATC TCCAGAGACA ACGCCAAGAA CTCCCTGTAT   240
CTGCAAATGA ACAGTCTGAG AGCTGAGGAT ACGGCCGTAT ATTACTGTGC GAAAGTCTCG   300
TACCTTAGCA CCGCGTCCTC CCTTGACTAT TGGGGCCAAG GTACCCTGGT CACCGTCTCG   360
AGT                                                                 363
```

---

What is claimed:

1. A method of reducing signs and symptoms in a patient with moderately to severely active rheumatoid arthritis, comprising:
   administering to said patient, in combination with methotrexate, a human anti-TNFα antibody,
   wherein the human anti-TNFα antibody is administered subcutaneously in a total body dose of 40 mg once every 13-15 days, and
   wherein the anti-TNFα antibody comprises an IgG1 heavy chain constant region; a variable light ("$V_L$") chain region comprising a CDR1 having the amino acid sequence of SEQ ID NO:7, a CDR2 having the amino acid sequence of SEQ ID NO:5, and a CDR3 having the amino acid sequence of SEQ ID NO:3; and a variable heavy ("$V_H$") chain region comprising a CDR1 having the amino acid sequence of SEQ ID NO:8, a CDR2 having the amino acid sequence of SEQ ID NO:6 and a CDR3 having the amino acid sequence of SEQ ID NO:4.

2. The method of claim 1, wherein the $V_L$ chain region of the anti-TNFα antibody has the amino acid sequence of SEQ ID NO:1 and the $V_H$ chain region of the anti-TNFα antibody has the amino acid sequence of SEQ ID NO:2.

3. The method of claim 1, wherein the dosage is administered from a 40 mg dosage unit form.

4. The method of claim 3, wherein the $V_L$ chain region of the anti-TNFα antibody has the amino acid sequence of SEQ ID NO:1 and the $V_H$ chain region of the anti-TNFα antibody has the amino acid sequence of SEQ ID NO:2.

\* \* \* \* \*